United States Patent
Gray et al.

(10) Patent No.: US 9,211,349 B2
(45) Date of Patent: Dec. 15, 2015

(54) MOLECULAR PROBES FOR MULTIMODALITY IMAGING OF ANIONIC MEMBRANE SURFACES

(71) Applicant: Molecular Targeting Technologies, Inc., West Chester, PA (US)

(72) Inventors: Brian Gray, Exton, PA (US); Kai Chen, San Gabriel, CA (US); Koon Y. Pak, Malvern, PA (US)

(73) Assignee: Molecular Targeting Technologies, Inc., West Chester, PA (US)

( * ) Notice: Subject to any disclaimer, the term of this patent is extended or adjusted under 35 U.S.C. 154(b) by 122 days.

(21) Appl. No.: 13/909,684

(22) Filed: Jun. 4, 2013

(65) Prior Publication Data

US 2013/0323172 A1    Dec. 5, 2013

Related U.S. Application Data

(60) Provisional application No. 61/655,755, filed on Jun. 5, 2012.

(51) Int. Cl.

| | | |
|---|---|---|
| *A61K 51/04* | (2006.01) | |
| *A61K 49/00* | (2006.01) | |
| *A61K 51/08* | (2006.01) | |
| *A61M 5/00* | (2006.01) | |
| *G01N 33/50* | (2006.01) | |
| *A61B 5/00* | (2006.01) | |
| *A61B 6/03* | (2006.01) | |

(52) U.S. Cl.
CPC ............. *A61K 51/044* (2013.01); *A61B 5/0035* (2013.01); *A61B 5/0059* (2013.01); *A61B 6/032* (2013.01); *A61K 49/0002* (2013.01); *A61K 49/0032* (2013.01); *A61K 49/0043* (2013.01); *A61K 51/0472* (2013.01); *A61K 51/08* (2013.01); *A61M 5/007* (2013.01); *G01N 33/5005* (2013.01); *A61B 6/037* (2013.01)

(58) Field of Classification Search
None
See application file for complete search history.

(56) References Cited

U.S. PATENT DOCUMENTS

| | | |
|---|---|---|
| 2008/0226562 A1 | 9/2008 | Groves et al. |
| 2010/0331542 A1 | 12/2010 | Smith |

FOREIGN PATENT DOCUMENTS

| | | |
|---|---|---|
| WO | 2010-028156 | 3/2010 |
| WO | 2011-019864 | 2/2011 |

OTHER PUBLICATIONS

Zhang et al. Annexin A5-conjugated polymeric micelles for dual SPECT and optical detection of apoptosis. 2011 J. Nucl. Med. 52: 958-964 plus Suppl Mat. Published online May 13, 2011.*
Li et al. Optimization of labeling dipicolylamine derivative, N,N'-(5-(4-aminobutoxy)-1,3-phenylene)bis(methylene)bis(1-(pyridin-2-yl)-N-(pyridin-2-ylmethyl)methanamine), with three 18F-prosthetic groups as potential imaging agents for metastatic infectious disease. 2012 J. Label Compd. Radiopharm. 55: 149-154.*
Lakshmi, C. et al., "Fluourophore-linked zinc(II)dipicolylamine coordination complexes as sensors for phosphatidylserine-containing membranes", Tedrahedron, 2004, vol. 60, pp. 11307-11315.
Wyffels, L. et al., Synthesis and preliminary evaluation of radiolabeled bis(zinc(II)-dypicolylamine) coordination complexes as cell death imaging agents:, Bioorganic & Medicinal Chemistry, 2011, vol. 19, pp. 3425-3433.

\* cited by examiner

*Primary Examiner* — Michael G Hartley
*Assistant Examiner* — Jennifer Lamberski
(74) *Attorney, Agent, or Firm* — Schwabe, Williamson & Wyatt

(57) ABSTRACT

Embodiments provide dual modality probes for imaging phosphatidylserine (PS) exposure and other anionic membrane surfaces. In various embodiments, the probes were constructed by utilizing a) the high selectivity of synthetic zinc (II) dipicolylamine coordination complexes (Zn-DPA) for targeting externalized PS which over-expresses in apoptotic and necrotic cells, b) a near-infrared (NIR) dye for optical imaging, and c) a widely used clinically approved radionuclide for PET (or SPECT) imaging. A variety of linking elements were incorporated into the probes between the Zn-DPA and radionuclide motif to modulate the pharmacokinetics. The in vitro and in vivo data of radiolabeled dipicolylamine probes demonstrated their utilities for imaging PS exposure with multiple imaging modalities.

13 Claims, 18 Drawing Sheets
(6 of 18 Drawing Sheet(s) Filed in Color)

US 9,211,349 B2

MOLECULAR PROBES FOR MULTIMODALITY IMAGING OF ANIONIC MEMBRANE SURFACES

CROSS REFERENCE TO RELATED APPLICATIONS

The present application claims priority to U.S. Provisional Patent Application No. 61/655,755, filed Jun. 5, 2012, entitled "MOLECULAR PROBES FOR MULTIMODALITY IMAGING OF ANIONIC MEMBRANE SURFACES," the disclosure of which is hereby incorporated by reference in its entirety.

TECHNICAL FIELD

Embodiments herein relate to the field of dual modality probes for imaging anionic membrane surfaces, and more specifically to synthetic zinc (II) dipicolylamine coordination complexes (Zn-DPA) having both a near-infrared (NIR) dye for optical imaging, and radionuclide for PET or SPECT imaging.

BACKGROUND

Fully quantitative imaging of target response to therapy offers the potential to provide early assessment of treatment efficacy, which may lead to individually tailored therapeutic plans and improved outcomes. Current guidelines for assessing the response of a target, such as a tumor, to therapy still rely heavily on measuring target volume via anatomical imaging. Thus, assessment of target response by CT scan or MRI is still the "gold standard" for target response evaluation. However, such anatomical changes are often delayed for weeks or months after initiation of treatment, and may not adequately reflect treatment efficacy. Real time non-invasive assessment of target response to treatment is therefore currently a major challenge in a wide variety of diseases, such as cancer and central nervous system diseases.

Detection of target-related cellular processes through molecular imaging may potentially address this need, and positron emission tomography (PET) with markers of glucose metabolism (e.g., $^{18}$F-fluorodeoxglocose; [$^{18}$F]-FDG), cell proliferation (e.g., 3'-deoxy-3'-$^{18}$F-fluorothymidine; [$^{18}$F]-FLT), or amino acid uptake (e.g., [$^{18}$F]-L-tyrosine) are increasingly utilized in oncological practice. All of these biomarkers detect molecular processes occurring in the viable cell, however they are limited by sub-optimal specificity, a small dynamic range of the observed changes, and/or limited applicability to slowly growing tumors.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Embodiments will be readily understood by the following detailed description in conjunction with the accompanying drawings. Embodiments are illustrated by way of example and not by way of limitation in the figures of the accompanying drawings.

DETAILED DESCRIPTION OF DISCLOSED EMBODIMENTS

Figure 1:
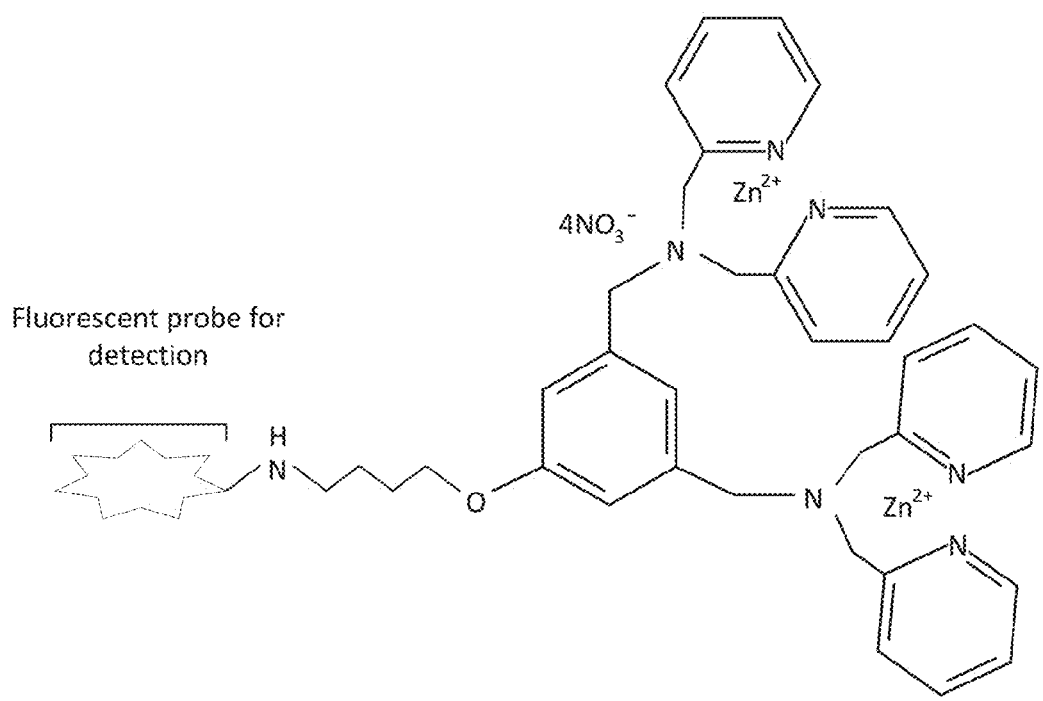
FIG. 1 illustrates a general structure of a fluorescently labeled bis-zinc-(II)-dipicolylamine (Zn-DPA) probe, where the Zn-DPA functionality has been found to bind strongly to phosphatidylserine (PS) residues, in accordance with various embodiments.

In the following detailed description, reference is made to the accompanying drawings which form a part hereof, and in which are shown by way of illustration embodiments that may be practiced. It is to be understood that other embodiments may be utilized and structural or logical changes may be made without departing from the scope. Therefore, the following detailed description is not to be taken in a limiting sense, and the scope of embodiments is defined by the appended claims and their equivalents.

Various operations may be described as multiple discrete operations in turn, in a manner that may be helpful in understanding embodiments; however, the order of description should not be construed to imply that these operations are order dependent.

The description may use perspective-based descriptions such as up/down, back/front, and top/bottom. Such descriptions are merely used to facilitate the discussion and are not intended to restrict the application of disclosed embodiments.

The terms "coupled" and "connected," along with their derivatives, may be used. It should be understood that these terms are not intended as synonyms for each other. Rather, in particular embodiments, "connected" may be used to indicate that two or more elements are in direct physical or electrical contact with each other. "Coupled" may mean that two or more elements are in direct physical or electrical contact. However, "coupled" may also mean that two or more elements are not in direct contact with each other, but yet still cooperate or interact with each other.

For the purposes of the description, a phrase in the form "NB" or in the form "A and/or B" means (A), (B), or (A and B). For the purposes of the description, a phrase in the form "at least one of A, B, and C" means (A), (B), (C), (A and B), (A and C), (B and C), or (A, B and C). For the purposes of the description, a phrase in the form "(A)B" means (B) or (AB) that is, A is an optional element.

The description may use the terms "embodiment" or "embodiments," which may each refer to one or more of the same or different embodiments. Furthermore, the terms "comprising," "including," "having," and the like, as used with respect to embodiments, are synonymous.

Embodiments herein provide dual modality pharmaceutical compounds that may be used to detect and/or monitor apoptosis in a cell or tissue. In various embodiments, the dual modality compounds include a small, non-protein phosphatidylserine (PS) affinity motif (for example, Zn-DPA) attached to both a radionuclide and a near-infrared (NIR) dye. In various embodiments, this combination may produce a probe that will allow multimodal imaging of PS exposure, and thus may be used for imaging tumors, bacterial infections, and inflammatory conditions. Combinations of imaging technologies (e.g., multimodality imaging) integrate the strengths of modalities, and eliminate one or more weaknesses of an individual modality, thus providing accurate and comprehensive anatomical and functional information simultaneously. In various embodiments, the strong affinity of Zn-DPA for PS may provide a novel targeting mechanism that takes advantage of differential lipid display patterns reported for treated targets versus untreated targets versus normal tissue.

Thus, in various embodiments, the dual modality compounds disclosed herein may be used to monitor a condition in a subject such as a tumor, an infection, or an inflammatory condition. By targeting PS, various embodiments of the disclosed compounds may be used for diagnosis and/or assessment of therapeutic efficacy in a number of conditions where PS is exposed, such as autoimmune diseases, metabolic diseases, cardiovascular diseases, neurodegenerative disorders and organ transplant rejection. In various embodiments, these compounds may be used, for example, to distinguish early responses to a treatment plan, for instance so that the treatment may be tailored to suit the individual patient. In other embodiments, such early monitoring may enable disease-modifying approaches that halt the use of ineffective drugs and institute alternative therapies, thereby achieving cost savings.

Positron emission tomography (PET) requires administration of probes labeled with positron-emitting radionuclides. Although some progress has been made in the development of target-specific PET tracers, there is no clinically approved PET tracer for PET imaging of cell death. Additionally, prior to the present disclosure, no dual-modality markers for cell death were known. The present compounds utilize "annexin-V mimic" technology to generate small molecule PS-targeted PET imaging agents, such as $^{18}$F-8b, that may be used in various applications to monitor apoptosis in cell and tissues, and to diagnose and monitor conditions involving PS expression.

In various embodiments, bis-zinc(II)-dipicolylamine (Zn-DPA) coordination complex technology may be employed to target to bio-membranes that contain anionic phospholipids. Based upon examination of the crystal structure of annexin-V bound to glycerol-phosphoserine, small molecule mimics of annexin-V may be designed, and fluorescent molecular probes containing two Zn-DPA units selectively stain the anionic membrane surfaces of apoptotic animal cells as opposed to the near-neutral membranes of healthy animal cells. An example is illustrated in FIG. 1, which shows a general structure of a fluorescently labeled bis-zinc-(II)-dipicolylamine (Zn-DPA) probe, where the Zn-DPA functionality has been found to bind selectively to phosphatidylserine (PS) residues, in accordance with various embodiments.

Figure 2:
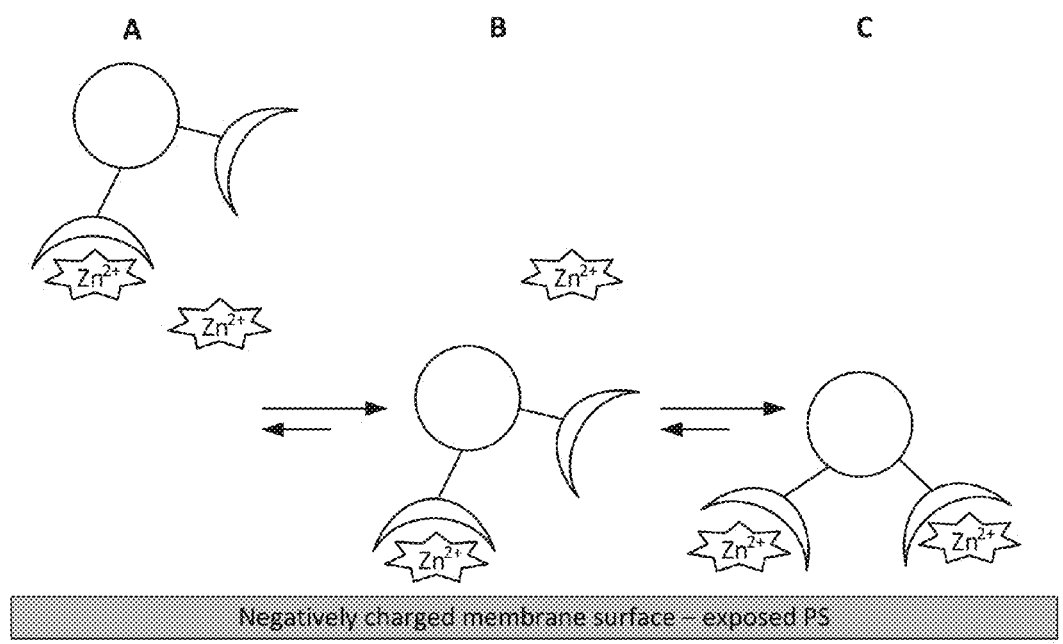
FIG. 2 illustrates a model of PS membrane binding in which the three component assembly process results in high affinity association of Zn-DPA molecules with PS-rich membranes, in accordance with various embodiments.

During apoptosis, the surface charge on the plasma membrane becomes increasingly negative due to appearance of anionic PS. FIG. 2 illustrates a model of PS membrane binding in which the three component assembly process results in high affinity association of Zn-DPA molecules with PS-rich membranes, in accordance with various embodiments. This binding model is very similar to that used by annexin-V, where the three-component assembly process involves the protein, $Ca^{2+}$ and PS-membrane. Under physiologic concentrations of $Zn^{2+}$ the predominant coordination complex is the mono-zinc species (species A) since first $Zn^{2+}$ has a binding constant of ~$10^{-7}$ M and the second ~$10^{-4}$ M. The binding of species A to the anionic PS exposed membrane (species B) would promote the binding of the second $Zn^{2+}$ with subsequent binding to the membrane forming a bivalently-bound species C. The association is driven primarily by electrostatic interactions with the bridging $Zn^{2+}$ cations.

Co-staining and blocking experiments with annexin-V-FITC reveals that the PS-affinity group (Zn-DPA) binds to the same membrane sites as annexin-V. Various fluorescent versions of these Zn-DPA compounds may be used to detect apoptosis in vitro, for instance using fluorescence microscopy and flow cytometry techniques. However, these single modality fluorescent probes cannot be used for imaging in an intact subject, for instance using PET imaging.

Although several radiolabeled probes have been reported previously for imaging anionic membrane surfaces, these probes have shown limited success. Because of their size and overall electrostatic charges, these probes possess undesirable clearance half-lives and display poor metabolic profiles. In addition, these probes can be used only in a single imaging modality. Thus, the imaging outcome obtained after administration of these probes is very limited.

By contrast, the dual modality probes disclosed herein provide for both robust fluorescence imaging as well as reliable radionuclide imaging, for example for the visualization of PS exposure and other anionic membrane surfaces. In various embodiments, the dual modality probes may be constructed by utilizing: a) the high selectivity of synthetic zinc (II) dipicolylamine coordination complexes (Zn-DPA) for targeting externalized PS which over-expresses in apoptotic and necrotic cells, b) a near-infrared (NIR) dye for optical imaging, and c) a widely used clinically approved radionuclide for PET (or SPECT) imaging.

Figure 6A:
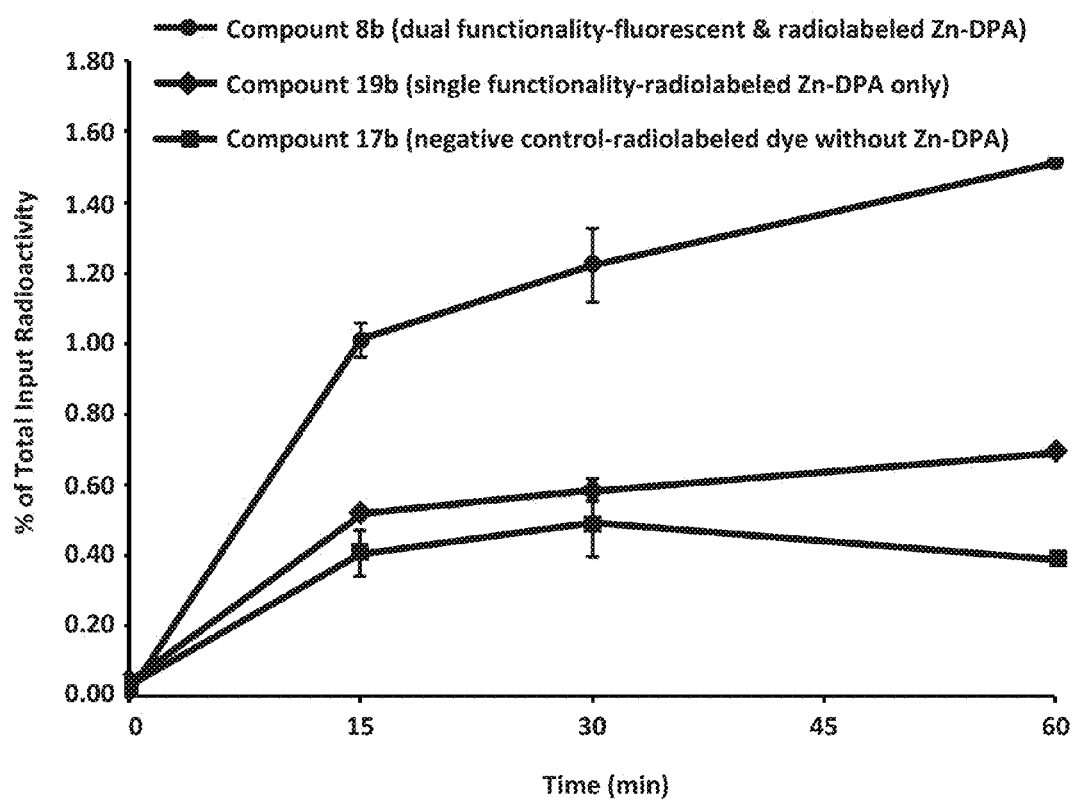
FIGS. 6A and 6B include a pair of graphs showing a comparison of a dual modality label with a single modality label, including the percentage of total input radioactivity versus time of incubation with paclitaxel-treated U87MG tumor cells (FIG. 6A), and the cell uptake ratio for compounds 8b, 19b, and 17b (FIG. 6B), in accordance with various embodiments.
Figure 6B:
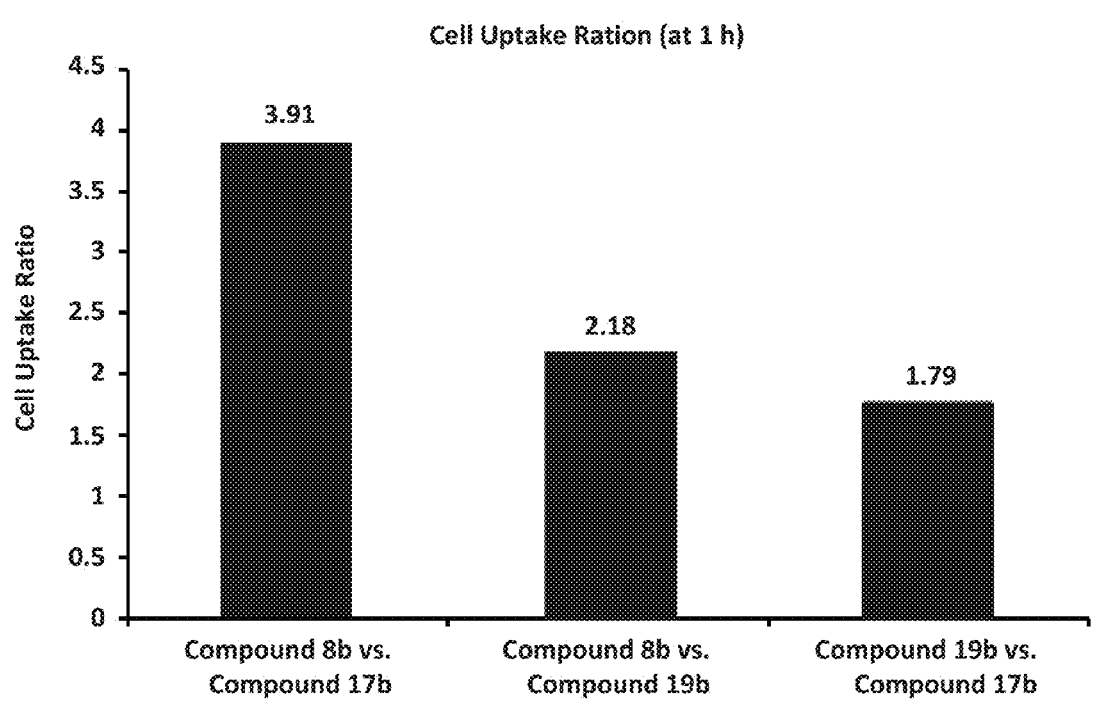

The dual-modality Zn-DPA probes described herein provide superior tumor cell uptake when compared to a comparable single modality Zn-DPA probe, such as a $^{18}F$—Zn-DPA probe. This is illustrated in FIGS. 6A and 6B, which include a pair of graphs showing a comparison of a dual modality label with a single modality label, including the percentage of total input radioactivity versus time of incubation with paclitaxel-treated U87MG tumor cells (FIG. 6A), and the cell uptake ratio for compounds 8b, 19b, and 17b (FIG. 6B). After one-hour incubation with paclitaxel-treated U87MG glioma cells, the tumor cell uptake of dual-modality Zn-DPA probe (8b) is 2.18-fold higher than that of single-modality Zn-DPA probe (19b). Moreover, the dual-modality Zn-DPA probes disclosed herein provide a superior signal to noise ratio in PET imaging when compared to a comparable single modality Zn-DPA probe, such as a $^{18}F$—Zn-DPA probe.

Figure 7A:
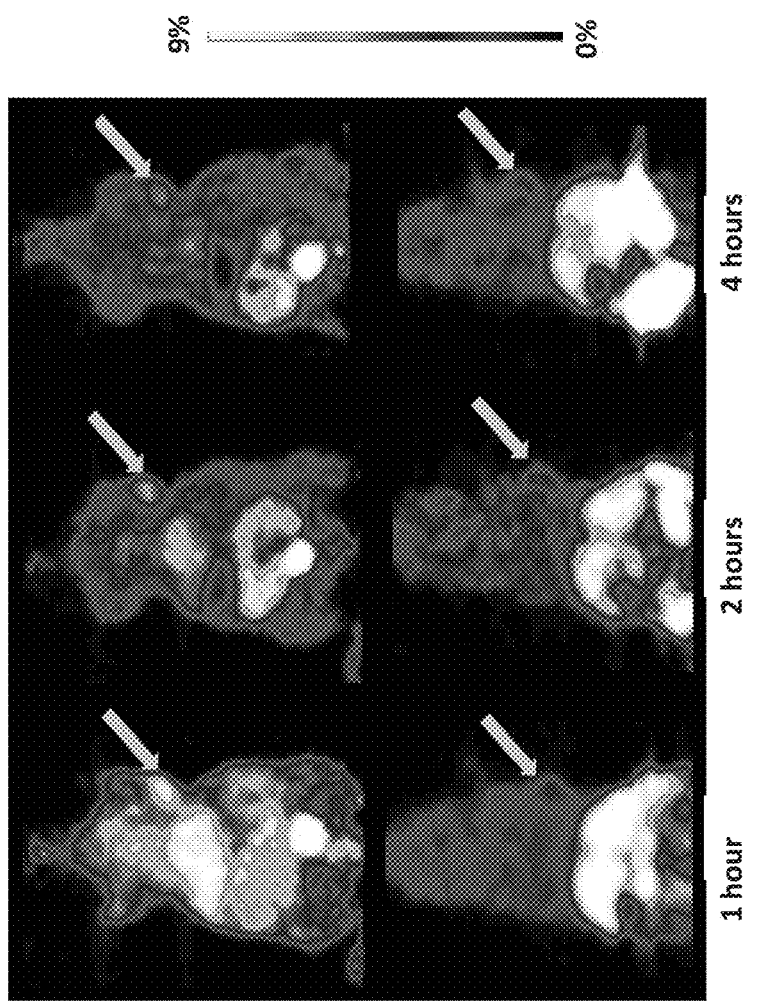
FIG. 7A shows decay-corrected whole-body coronal microPET images of nude mice bearing U87MG tumor (n=5/group) at 1, 2, and 4 hours post-injection of 8b (7.4 MBq) verses compound (19b) (7.4 MBq), with tumors indicated by arrows, in accordance with various embodiments.
Figure 7B:
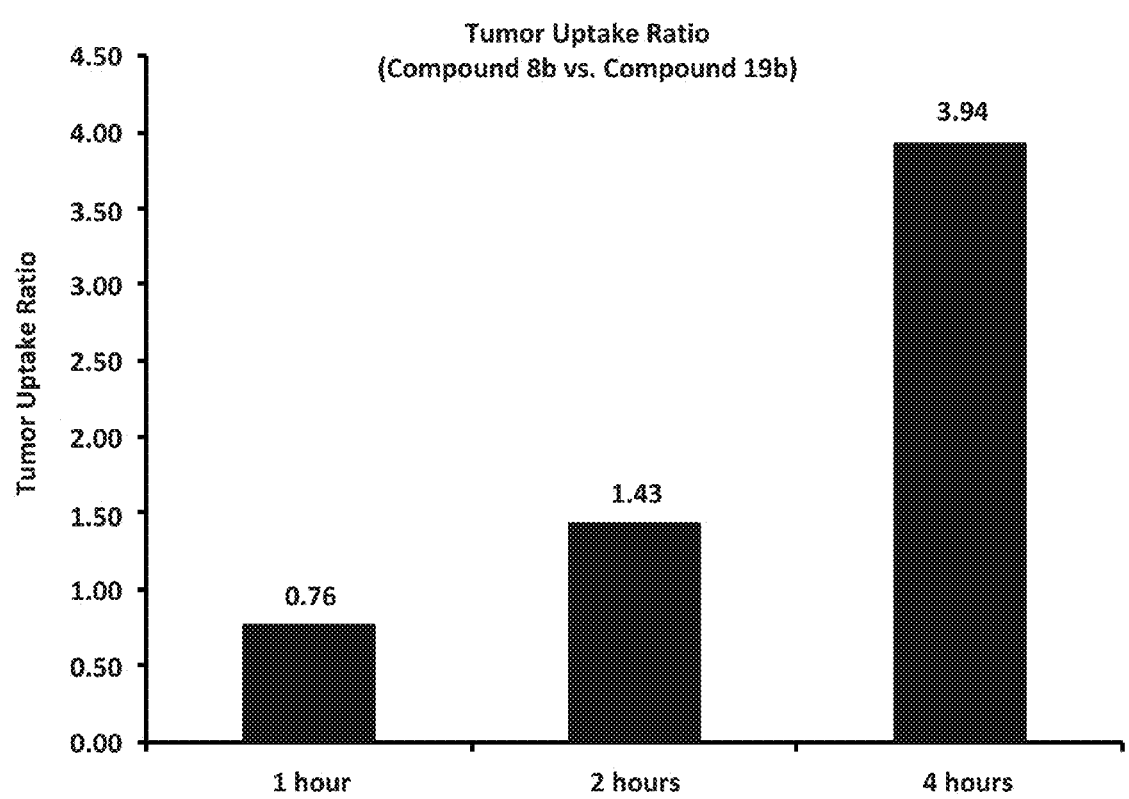
FIG. 7B shows the tumor uptake ratio of compound 8b versus compound 19b in the mice shown in FIG. 7A, in accordance with various embodiments.

As illustrated in FIG. 7A, before the daily combination treatment of All-Trans Retinoic Acid (ATRC) (1.5 µg/kg) and Paclitaxel (45 µg/kg), the dual-modality Zn-DPA probe 8b demonstrated significantly higher U87MG tumor uptake when compared to the single-modality Zn-DPA probe 19b. The tumor uptake of 8b is 1.43-fold higher than that of 19b at 2 hours post-injection, and about 4-fold higher than that of 19b at 4 hours post-injection as shown in FIG. 7B. This improved functionality could not have been predicted from the structure of the compounds alone, and it enables the clinical use of the dual modality compounds in a variety of applications.

Figure 8A:
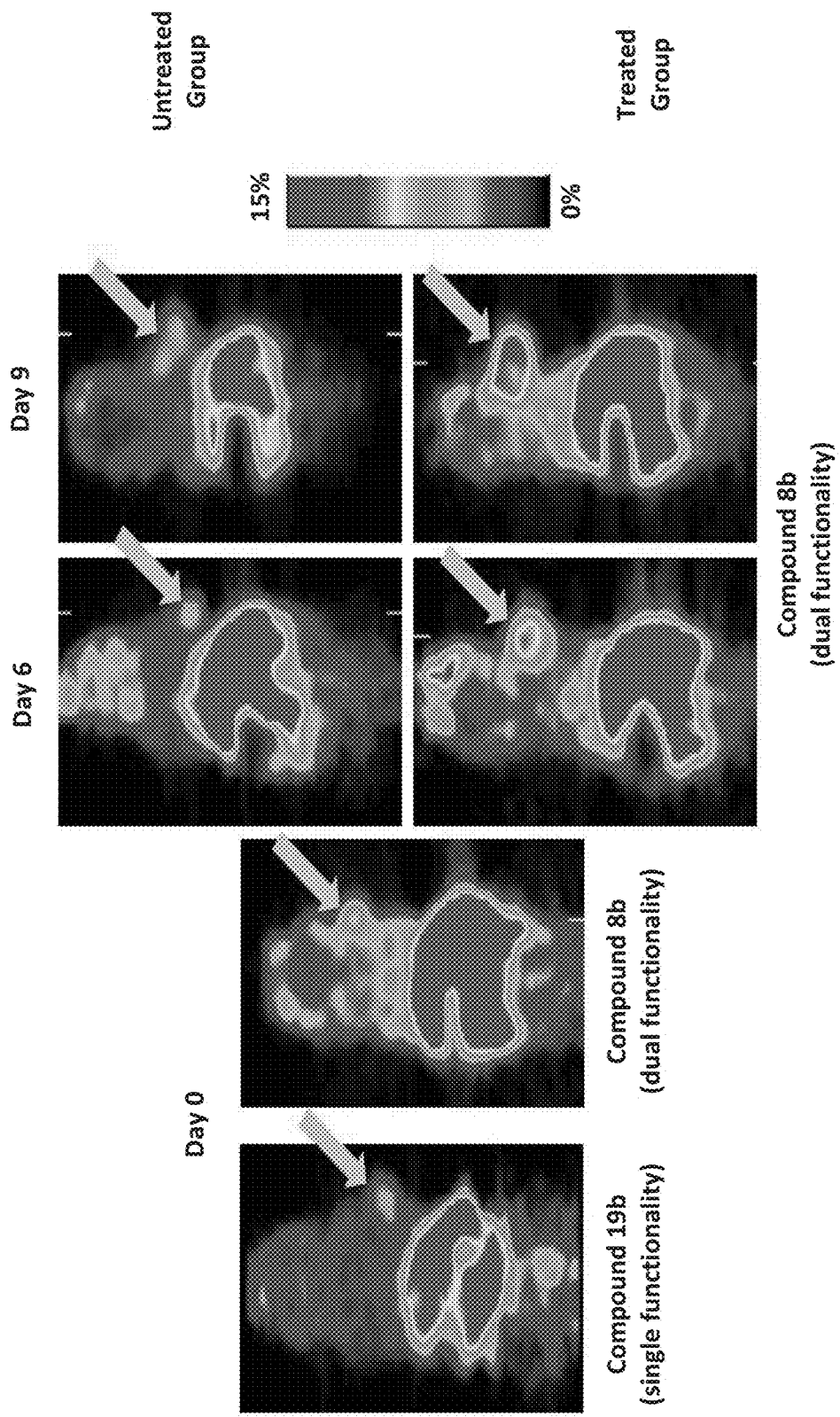
FIG. 8A includes a series of panels illustrating decay-corrected whole-body coronal microPET images of nude mice bearing U87MG tumor (n=6/group) at 2 hours post-injection of 8b (7.4 MBq) or 19b (7.4 MBq) before and after the daily combination treatment of All-Trans Retinoic Acid (ATRC) (1.5 µg/kg) and Paclitaxel (45 µg/kg), with tumors indicated by arrows, in accordance with various embodiments.
Figure 8B:
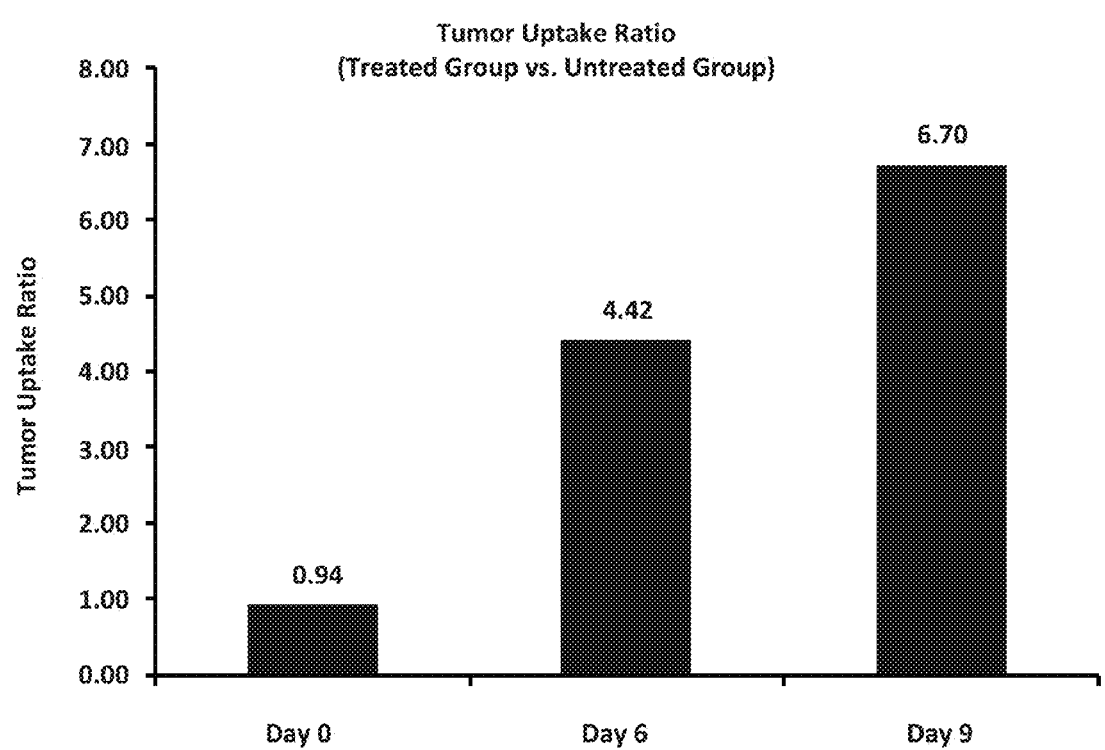
FIG. 8B illustrates the tumor uptake ratio of a treated group versus an untreated group at 2 hours post-injection of 8b (7.4 MBq), in accordance with various embodiments.

FIG. 8A includes a series of panels illustrating decay-corrected whole-body coronal microPET images of nude mice bearing U87MG tumor (n=6/group) at 2 hours post-injection of 8b (7.4 MBq) or 19b (7.4 MBq) before and after the daily combination treatment of All-Trans Retinoic Acid (ATRC) (1.5 µg/kg) and Paclitaxel (45 µg/kg), with tumors indicated by arrows, and FIG. 8B illustrates the tumor uptake ratio of the treated group versus the untreated group at 2 hours post-injection of 8b (7.4 MBq). Thus, as illustrated in FIG. 8A, the dual-modality Zn-DPA probe 8b demonstrated increasing U87MG tumor uptake on Day 6 and Day 9 after the daily combination treatment of ATRC (1.5 µg/kg) and Paclitaxel (45 µg/kg) when compared to the pretreatment (Day 0), whereas the U87MG tumor uptake of 8b retained with minimal changes in the untreated group. As illustrated in FIG. 8B, the U87MG tumor uptake of 8b in the treated group was about 4.42-fold higher than that in the untreated group on Day 6. On Day 9, the U87MG tumor uptake ratio of 8b in the treated group versus the untreated group reached 6.70.

Figure 9A:
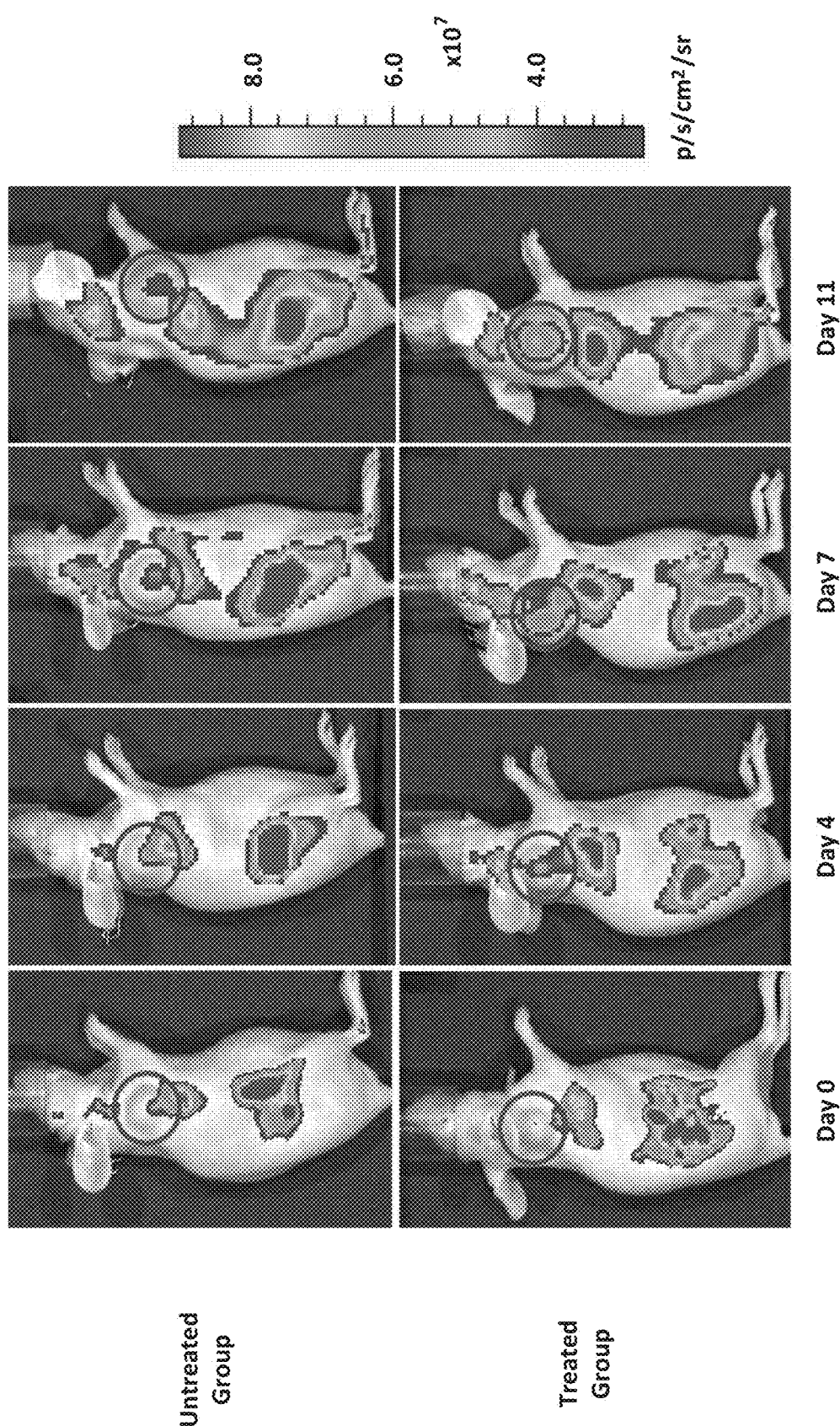
FIG. 9A includes a series of panels illustrating In vivo near-infrared fluorescence images of nude mice bearing U87MG tumor (n=6/group) at 4 hours post-injection of 8a before and after the daily combination treatment of ATRC (1.5 µg/kg) and Paclitaxel (45 µg/kg), with tumors indicated by red circles, in accordance with various embodiments.
Figure 9B:
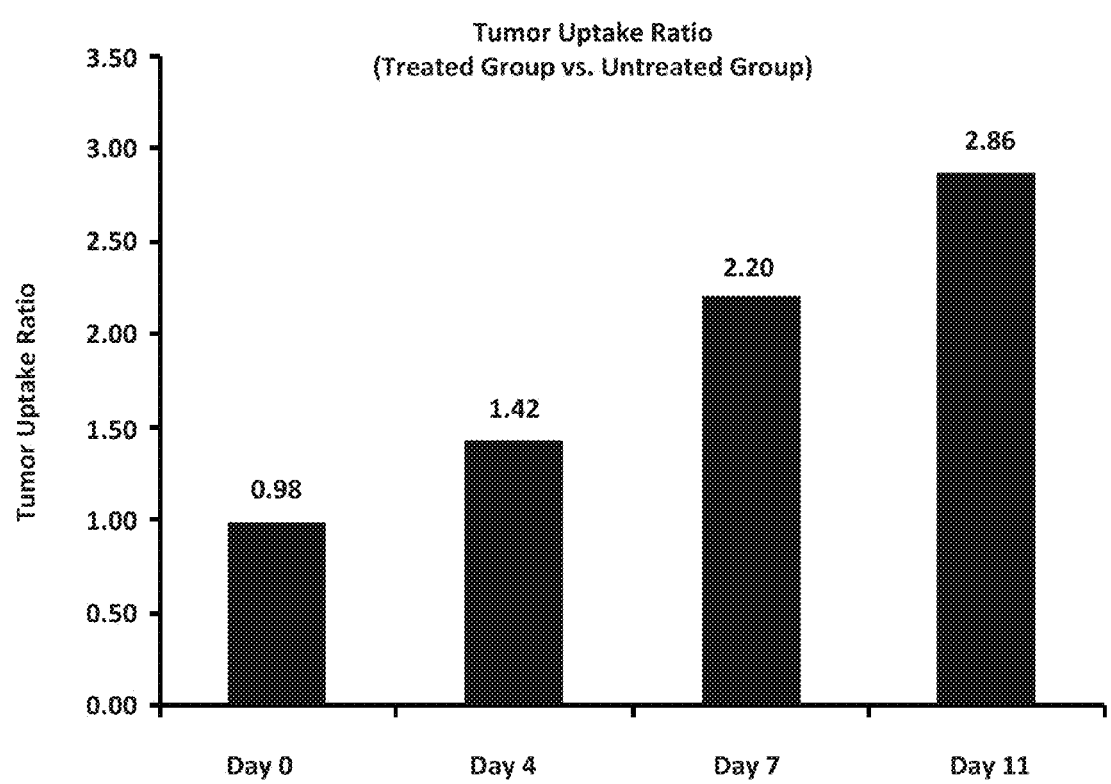
FIG. 9B illustrates the tumor uptake ratio of a treated group versus an untreated group at 4 hours post-injection of 8a, in accordance with various embodiments.

FIG. 9A includes a series of panels illustrating In vivo near-infrared fluorescence images of nude mice bearing U87MG tumor (n=6/group) at 4 hours post-injection of 8a before and after the daily combination treatment of ATRC (1.5 µg/kg) and Paclitaxel (45 µg/kg), with tumors indicated by circles, and FIG. 9B illustrates tumor uptake ratio of the treated group versus the untreated group at 4 hours post-injection of 8a. As illustrated in FIG. 9A, compound 8a demonstrated increasing U87MG tumor uptake for optical imaging on Days 4, 7, and 9 after the daily combination treatment of ATRC (1.5 µg/kg) and Paclitaxel (45 µg/kg) when compared to the untreated group. As illustrated in FIG. 9B, on Day 4, 7, and 9, the U87MG tumor uptake ratios of 8a in the treated group versus the untreated group are 1.42, 2.20, and 2.86, respectively. In some embodiments, a linking element may be incorporated into the probe between the Zn-DPA and radionuclide motif, for instance, if modulation the pharmacokinetics is desired.

The following Examples are provided for illustration of various embodiments, and are not intended to be construed as limiting.

EXAMPLES

Example 1

Figure 10:
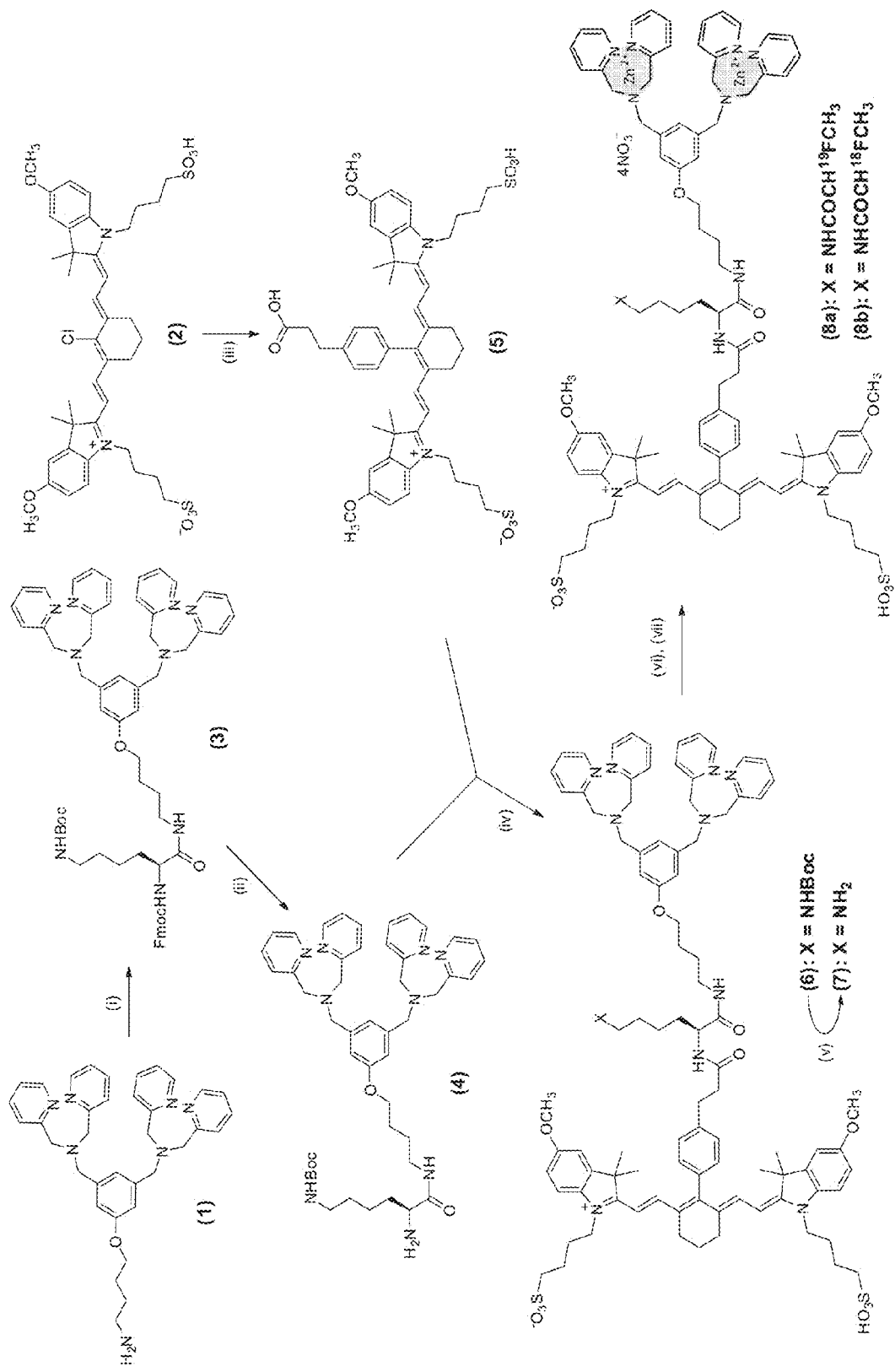
FIG. 10 illustrates Synthetic Scheme 1, which may be used to prepare non-radioactive and radioactive fluorine-containing tracers with a short butyl linking element, in accordance with various embodiments.

Exemplary Reaction Schemes for Forming an Analog of Radiolabeled Dipicolylamine Derivatives, Part One This Example illustrates methods that may be used in various embodiments for the synthesis of non-radioactive and radioactive fluorine-containing fluorescent compounds (8a) and (8b). In various embodiments, compounds in accordance with the present disclosure may be synthesized according to Synthetic Scheme 1. FIG. 10 illustrates Synthetic Scheme 1, which may be used to prepare non-radioactive and radioactive fluorine-containing tracers with a short butyl linking element, in accordance with various embodiments. In the illustrated scheme, the reagents include the following: (i) Fmoc-Lys (Boc)-OPfp, DMF (ii) piperidine, DMF (iii) 4-(2-carboxyethyl)phenylboronic acid, tetrakis(triphenylphosphine)Pd (0), triethylamine (iv) HBTU, DMF, DIPEA (v) 60% TFA in DCM (vi) 2-fluoropropionic acid nitrophenyl ester, $CH_3CN$ (vii) $Zn(NO_3)_2$.

In various embodiments, compounds (1) and (2) may be prepared via procedures known to those of skill in the art (see, e.g., Lakshmi et al., (2004) *Tetrahedron*, 60, 11307-11315; Narayanan & Patonay (1995) *J. Org. Chem.* 60, 2391-2395).

Synthesis of (3)

A solution of (1) (215 mg, 0.366 mmol) and Fmoc-Lys (Boc)-OPfp (260 mg, 0.410 mmol, BAChem) in 3 mL of DMF was stirred overnight at room temperature. The solution was then concentrated and purified by silica gel column chromatography eluting with 4% ammonium hydroxide in $CH_3CN$ and then 5% ammonium hydroxide in $CH_3CN$ to provide 281 mg of (3) as a pale yellow oil. $^1H$ NMR ($CDCl_3$, 400 MHz): δ 8.51 (d, 4H, J=4.6 Hz), 7.75 (d, 2H, J=7.5 Hz), 7.65-7.54 (m, 9H), 7.38 (t, 2H, J=7.5 Hz), 7.30 (d, 1H, J=8.4 Hz), 7.18-7.11 (m, 4H), 7.07 (s, 1H), 6.83 (s, 2H), 6.34-6.24 (m, 1H), 5.59-5.50 (m, 1H), 4.73-4.60 (m, 1H), 4.47-4.36 (m, 2H), 4.20 (t, 1H, J=6.8 Hz), 4.13-4.05 (m, 1H), 3.95 (t, 2H, J=5.8 Hz), 3.80 (s, 8H), 3.64 (s, 4H), 3.39-3.24 (m, 2H), 3.16-3.00 (m, 2H), 1.93-1.78 (m, 2H), 1.75-1.59 (m, 2H), 1.54-1.32 (m, 9H).

Synthesis of (4)

Treatment of (3) with a solution of piperidine in DMF (1:3) overnight followed by solvent concentration furnished a crude material. Purification was carried out by silica gel chromatography using an increasing concentration of ammonium hydroxide (2-10%) in $CH_3CN$ provided 217 mg of pure (4). $^1$H NMR ($CDCl_3$, 400 MHz): δ 8.51 (d, 4H, J=4.9 Hz), 7.68-7.55 (m, 8H), 7.17-7.10 (m, 4H), 7.06 (s, 1H), 6.84 (s, 2H), 4.68-4.58 (m, 1H), 3.97 (t, 2H, J=6.0 Hz), 3.80 (s, 8H), 3.65 (s, 4H), 3.40-3.28 (m, 3H), 3.16-3.06 (m, 2H), 1.92-1.79 (m, 3H), 1.76-1.66 (m, 2H), 1.57-1.47 (m, 3H), 1.46-1.42 (m, 9H).

Synthesis of (5)

To a solution of (2) (0.50 g, 0.636 mmol) in methanol (10 mL) and water (2.5 mL) was added tetrakis(triphenylphosphine)Pd(0) (89 mg, 0.775 mmol) and 4-(2-carboxyethyl)phenylboronic acid (0.27 g, 1.41 mmol) followed by triethylamine (1.25 mL). The resulting solution was stirred at room temperature overnight and then purified by silica gel chromatography eluting with an increasing amount of methanol in dichloromethane (5% to 30%) to provide pure (5; 400 mg, 64%). $^1$H NMR (DMSO-$d_6$, 400 MHz): δ 7.47 (d, 2H, J=7.9 Hz), 7.28 (d, 2H, J=8.9 Hz), 7.18-7.10 (m, 4H), 7.07 (d, 2H, J=14.0 Hz), 6.90 (dd, 2H, J=2.3, 6.4 Hz), 6.14 (d, 2H, J=14.1 Hz), 4.21-3.99 (m, 6H), 3.76 (s, 6H), 2.71-2.58 (m, 6H), 2.46 (t, 4H, J=7.2 Hz), 2.00-1.86 (m, 2H), 1.80-1.59 (m, 8H), 1.10 (s, 12H). ESI-MS m/z $C_{49}H_{59}N_2O_{10}S_2$ calcd, 900.37. Found, 901.50 [M+H]$^+$.

Synthesis of (6)

To a solution of (4) (54 mg, 0.066 mmol) in DMF (2 mL) was added a solution of (5) (60 mg, 0.667 mmol) in anhydrous DMSO then solid HBTU (32 mg, 0.084 mmol) and a few drops of DIPEA. The resulting solution was stirred at room temperature for 1 hour. The reaction mixture was then purified by silica gel chromatography eluting with 20% methanol in dichloromethane and then gradually increasing the methanol to 25% and ammonium hydroxide from 0 to 3% to provide 75 mg of (6). $^1$H NMR (DMSO-$d_6$, 400 MHz): δ 8.48 (d, 4H, J=4.0 Hz), 7.78-7.70 (m, 4H), 7.57 (d, 4H, J=7.8 Hz), 7.44 (d, 2H, J=8.0 Hz), 7.31-7.20 (m, 6H), 7.15-7.10 (m, 4H), 7.08 (s, 2H), 7.04 (s, 1H), 6.89 (dd, 2H, J=6.4, 2.4 Hz), 6.80 (s, 2H), 6.13 (d, 2H, J=14.2 Hz), 4.09-4.01 (m, 4H), 3.93 (t, 2H, J=6.3 Hz), 3.74 (s, 6H), 3.70 (s, 8H), 3.58 (s, 4H), 3.17 (d, 2H, J=5.2 Hz), 3.01-2.93 (m, 2H), 2.91-2.83 (m, 2H), 2.69-2.61 (m, 4H), 2.46 (t, 4H, J=7.2 Hz), 1.98-1.87 (m, 2H), 1.78-1.60 (m, 8H), 1.60-1.48 (m, 2H), 1.34 (s, 12H), 1.30-1.18 (m, 10H), 1.11-1.01 (m, 9H).

Synthesis of Compound (7)

Compound (6) (70 mg) was stirred in a solution of TFA:$CH_2Cl_2$ (60:40) at room temperature for 6 hours, then concentrated to provide (7). ESI-MS m/z $C_{91}H_{111}N_{11}O_{11}S_2$ calcd, 1,597.79. Found, 1,598.75 [M+H]$^+$, 800.24 [M+2H]$^{2+}$.

Synthesis of (8a)

2-fluoropropionic acid (9.6 mg, 0.104 mmol), disuccinimidyl carbonate (100 mg, 0.390 mmol), and triethylamine (55 µL) were stirred together in anhydrous DMF (1 mL) for 22 hours. Compound (7) (50 mg, 0.0313 mmol) in DMF (0.5 mL) containing triethylamine (50 uL) was then added and the mixture stirred for 45 minutes. The reaction mixture was then concentrated and purified via reverse-phase HPLC to provide (8a). ESI-MS m/z $C_{94}H_{114}FN_{11}O_{12}S_2$ calcd, 1,671.81. Found, 1,672.76 [M+H]$^+$, 837.28 [M+2H]$^{2+}$.

Example 2

Exemplary Reaction Schemes for Forming an Analog of Radiolabeled Dipicolylamine Derivatives, Part Two This Example illustrates methods for a synthetic scheme that may be used in various embodiments to prepare non-radioactive and radioactive fluorine containing fluorescent tracers with polyethylene glycol (PEG) and/or amino acid (AA) linking elements. In various embodiments, the incorporation of different linkers may affect the overall hydrophilic/hydrophobic balance of small molecules. Thus, in various embodiments, achieving the correct hydrophilic/hydrophobic balance may be critical to obtaining favorable pharmacokinetics and target/background (T/B) ratios. In addition to tracer (8b), which has a short lipophilic butyl linker, other types of pharmacokinetic modifying groups, such as polyethylene glycol units or amino acid sequences may be incorporated into the dual modality tracer. For example, in various embodiments, the $PEG_4$ linker may increase tracer hydrophilicity while preserving overall charge, and may improve tumor uptake and excretion kinetics of various small peptide receptor-targeted radiopharmaceuticals. As another example, the $Asp_2$ amino acid linker may enhance hydrophilicity and also modify charge (e.g., introduce two negative carboxyl groups), and this type of modification may reduce accumulation of renal radioactivity.

Figure 11:
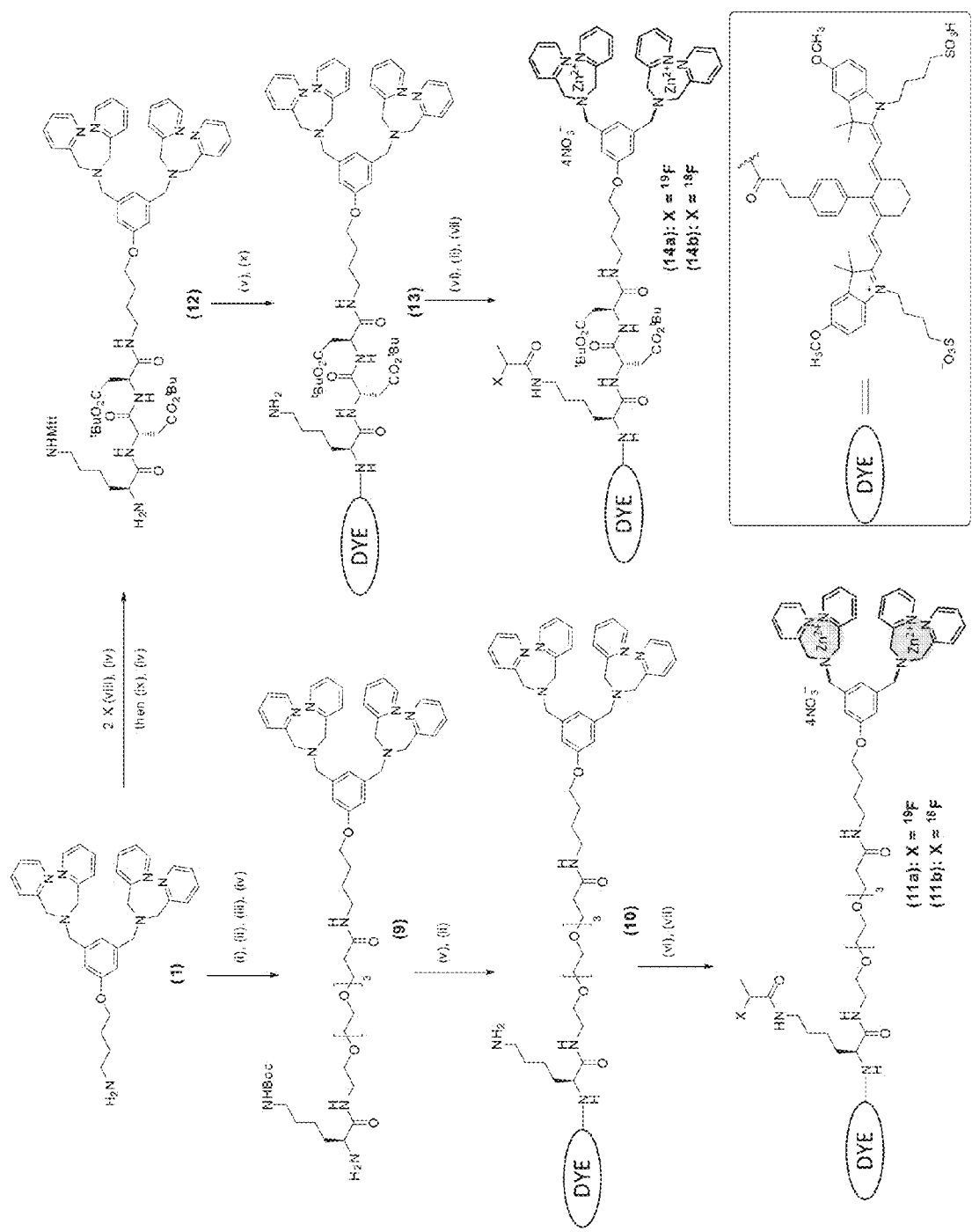
FIG. 11 illustrates Synthetic Scheme 2, which may be used to prepare non-radioactive and radioactive fluorine containing fluorescent tracers with PEG and AA linking elements, in accordance with various embodiments.

FIG. 11 illustrates Synthetic Scheme 2, which may be used to prepare non-radioactive and radioactive fluorine containing fluorescent tracers with PEG and AA linking elements, in accordance with various embodiments. For instance, in various embodiments, the $^{19}$F reference compounds (11a) and (14a) may be prepared as shown in Synthetic Scheme 2. In the illustrated scheme, the reagents include: (i) BocNH($CH_2CH_2O)_4$—$CH_2$—$CH_2CO_2H$, EDC, DMF (ii) 50% TFA in DCM (iii) Fmoc-Lys(Boc)-OPfp, DMF (iv) piperidine (v) (5)-NHS, DMF (vi) 2-fluoropropionic acid nitrophenyl ester, $CH_3CN$ (vii) $Zn(NO_3)_2$ (viii) Fmoc-Asp(OtBu)-NHS, DMF (ix) Fmoc-Lys(Mtt)-OH, NHS, HOBt, DCC (x) 1% TFA in DCM. Compound (I) was coupled with the $PEG_4$ derivative, BocNH($CH_2CH_2O)_4CH_2$-$CH_2CO_2H$ (Quanta Biodesign, Inc.) under standard peptide coupling conditions. Removal of the Boc protecting group with TFA followed by coupling with the lysine analog, Fmoc-Lys(Boc)-OPfp, and subsequent removal of the Fmoc protecting group with piperidine may then furnish (9). Carboxylic acid dye (5) may be coupled to (9) under standard conditions, followed by the Boc group removal to provide (10). Reaction of (10) with [$^{19}$F]NFP [45] followed by chromatographic purification and addition of 2.1 equivalents of zinc nitrate may provide (11a). Preparation of (14a) initially involves 3 cycles of standard amino acid coupling/deprotection reactions with (1), using Fmoc-Asp (OtBu)-NHS (2 cycles), then Fmoc-Lys(Mtt)-NHS to provide (12). Coupling of (12) with carboxylic acid dye (5) followed by selective removal of the Mtt protecting group may provide amine (13). The 2-fluoropropionyl group may be incorporated as before, then the t-Butyl groups may be quickly removed (TFA, 30 minutes, room temperature) and zinc added to provide (14a).

Synthesis of Radioactive $^{18}$F-Labeled Fluorescent Tracers (8b), (11b) and (16b)

The radiosynthesis of [$^{18}$F]NFP was performed as previously described (see, e.g., Chin et al., (2012) *Mol. Imaging. Biol.* 14, 88-95). About 1 mg of (7) [or (10); or (13)] in 0.1 mL of DMSO containing 20 µL of diisopropylethylamine was added to the [$^{18}$F]NFP-containing vial and heated at 80° C. for 10 minutes. The mixture was then cooled and diluted with 0.7 mL of water containing 25 µL of acetic acid and loaded onto a semi-prep HPLC column [in the case of (13) a TFA treatment was added to remove t-Butyl groups]. The desired product was collected, concentrated, and incubated with 100 µL of 4.2 mM zinc nitrate at 40° C. for 10 minutes. The final product was passed through a 0.22-µm Millipore filter into a sterile dose vial for use.

Example 3

Figure 12:
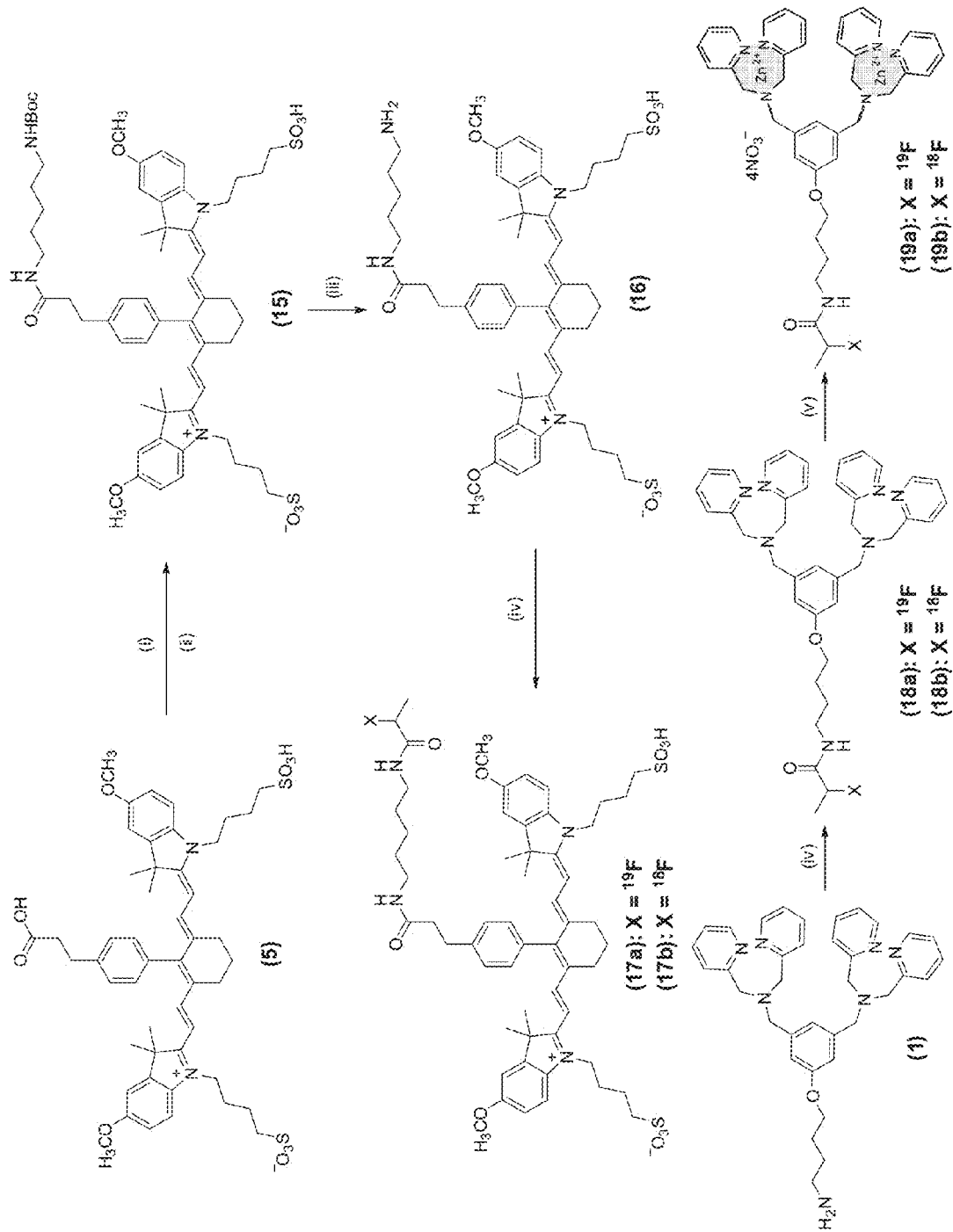
FIG. 12 illustrates Synthetic Scheme 3, which may be used to prepare non-radioactive and radioactive fluorine containing control compounds, in accordance with various embodiments.

Exemplary Reaction Schemes for Forming an Analog of Radiolabeled Dipicolylamine Derivatives, Part Three This Example illustrates synthetic schemes that may be used to form analogs of radiolabeled dipicolylamine derivatives in various embodiments. FIG. 12 illustrates Synthetic Scheme 3, which may be used to prepare non-radioactive and radioactive fluorine containing control compounds, in accordance with various embodiments. In the illustrated scheme, the reagents include: (i) NHS, DCC, DMF (ii) BocNH(CH$_2$)$_5$NH$_2$ (iii) 10% TFA in DCM (iv) 2-fluoropropionic acid nitrophenyl ester (v) zinc nitrate.

Synthesis of Non-Radioactive $^{19}$F-Control Compounds (17a) and (18a)

Preparation of (15)

To a solution of dye (5) (100 mg, 0.111 mmol) in 2 mL of DMF was added N-hydroxysuccinimide (76 mg, 0.666 mmol) followed by N,N'-dicyclohexylcarbodiimide (134 mg, 0.666 mmol) in 2 mL of DMF. The solution was stirred at room temperature overnight. N-Boc-cadaverine (70 µL) in 1 mL of DMF was then added and the mixture stirred for 1 hour and concentrated. The product was purified by silica gel chromatography eluting with increasing amounts of methanol (5% to 35%) in dichloromethane to yield 90 mg of (15). $^1$H NMR (DMSO-d$_6$, 400 MHz): δ 7.44 (d, 2H, J=7.7 Hz), 7.28 (d, 2H, J=8.8 Hz), 7.18-7.02 (m, 6H), 6.90 (dd, 2H, J=6.6, 2.0 Hz), 6.14 (d, 2H, J=14.1 Hz), 4.14-4.00 (m, 4H), 3.76 (s, 6H), 3.14-3.04 (m, 2H), 3.02-2.93 (m, 2H), 2.93-2.84 (m, 2H), 2.71-2.61 (m, 4H), 2.48-2.42 (m, 6H), 1.98-1.87 (m, 2H), 1.79-1.62 (m, 10H), 1.37 (s, 9H), 1.30-1.20 (m, 4H), 1.11 (s, 12H).

Preparation of (16)

Compound (15) (90 mg, 0.083 mmol) was dissolved in 5 mL of solution (10% TFA:90% CH$_2$Cl$_2$) and stirred at room temperature for 2 hours. The reaction mixture was then concentrated and placed in a vacuum oven at 50° C. for a few hours to dry to provide (16). ESI-MS m/z C$_{54}$H$_{72}$N$_4$O$_9$S$_2$ calcd, 984.47. Found, 985.63 [M+H]$^+$, 493.27 [M+2H]$^{2+}$.

Preparation of (17a)

To a solution of 2-fluoropropionic acid (7.8 mg, 84.5 µmol) in 0.5 mL anhydrous acetonitrile was added TSTU (17.6 mg, 58.5 µmol). The pH of the solution was adjusted to 8.5-9.0 by DIPEA. The reaction mixture was stirred at room temperature for 0.5 hours, and then compound (16) (3 µmol) in DMF was added in one aliquot. After being stirred at room temperature for 2 hours, the product was isolated by semi-preparative HPLC to provide (17a). ESI-MS m/z C$_{57}$H$_{75}$FN$_4$O$_{10}$S$_2$ calcd, 1,058.49. Found, 1059.53 [M+H]$^+$.

Preparation of (18a)

To a solution of 2-fluoropropionic acid (7.8 mg, 84.5 µmol) in 0.5 mL anhydrous acetonitrile was added TSTU (17.6 mg, 58.5 µmol). The pH of the solution was adjusted to 8.5-9.0 by DIPEA. The reaction mixture was stirred at room temperature for 0.5 hours, and then compound (I) (3 µmol) in DMF was added in one aliquot. After being stirred at room temperature for 2 hours, the product was isolated by semi-preparative HPLC to provide (18a). ESI-MS m/z C$_{39}$H$_{44}$FN$_7$O$_2$ calcd, 661.35. Found, 662.43 [M+H]$^+$, 684.42 [M+Na]$^+$.

Synthesis of $^{18}$F-Control Compounds (17b) and (19b)

Preparation of (17b)

About 1 mg of (16) in 0.1 mL of DMSO containing 20 µL of diisopropylethylamine was added to the [$^{18}$F]NFP-containing vial and heated at 80° C. for 10 minutes. The mixture was then cooled and diluted with 0.7 mL of water containing 25 µL of acetic acid and loaded onto a semi-prep HPLC column. The desired product was collected, concentrated, and passed through a 0.22-µm Millipore filter into a sterile dose vial for use.

Preparation of (19b)

About 1 mg of (1) in 0.1 mL of DMSO containing 20 µL of diisopropylethylamine was added to the [$^{18}$F]NFP-containing vial and heated at 80° C. for 10 minutes. The mixture was then cooled and diluted with 0.7 mL of water containing 25 µL of acetic acid and loaded onto a semi-prep HPLC column. The desired product was collected, concentrated, and incubated with 100 µL of 4.2 mM zinc nitrate at 40° C. for 10 minutes. The final product was passed through a 0.22-µm Millipore filter into a sterile dose vial for use.

Example 4

Figure 13:
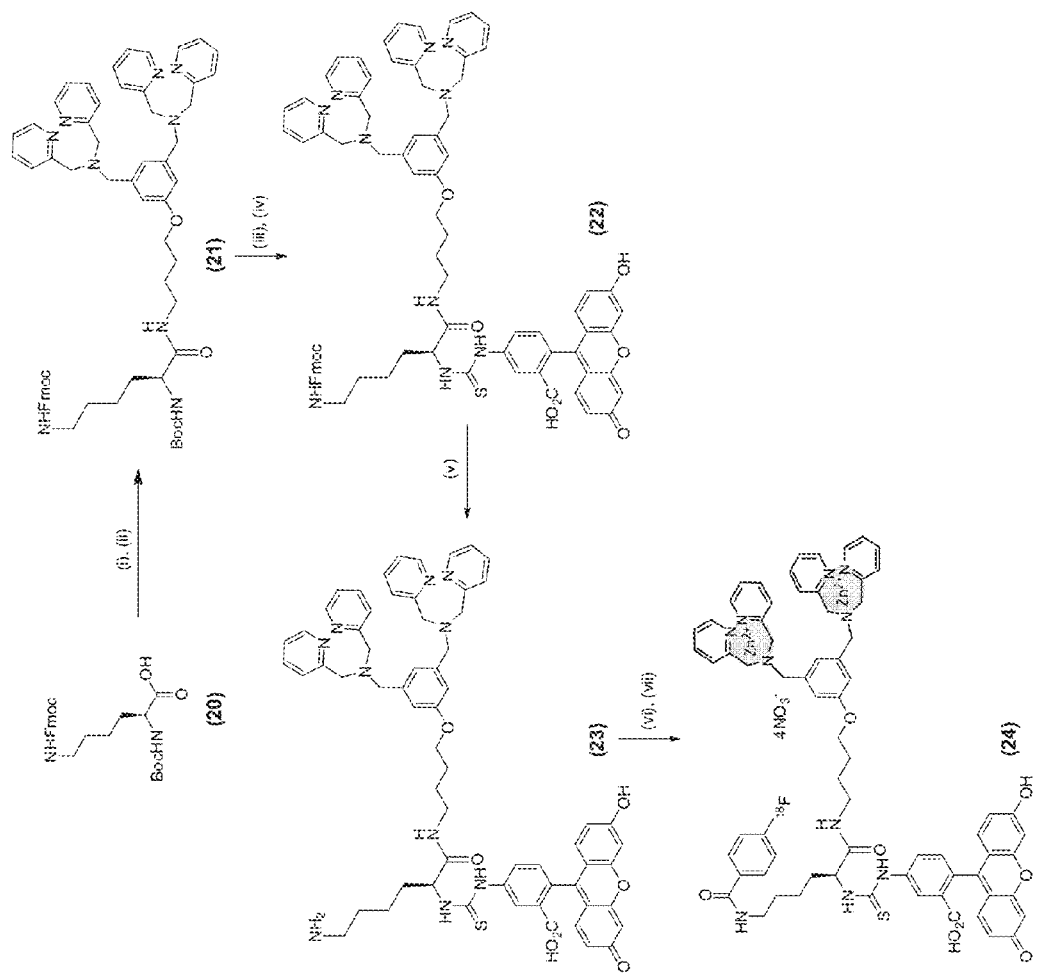
FIG. 13 illustrates Synthetic Scheme 4, which may be used to prepare a dual modality tracer with radioactive fluorine for PET imaging and fluorescein for optical imaging, in accordance with various embodiments.

Exemplary Reaction Schemes for Forming an Analog of Radiolabeled Dipicolylamine Derivatives, Part Four This example illustrates methods that may be used to prepare dual tracers containing radioactive fluorine and the fluorescent dye, fluorescein. In various embodiments, compounds in accordance with the present disclosure may be synthesized according to Synthetic Scheme 4. FIG. 13 illustrates Synthetic Scheme 4, which may be used to prepare a dual modality tracer with radioactive fluorine for PET imaging and fluorescein for optical imaging, in accordance with various embodiments. In the illustrated scheme, the reagents include: (i) DCC, NHS (ii) (1) (iii) TFA (iv) FITC (v) Piperidine (vi) $^{18}$F-SFB (vii) 2 equiv. Zn(NO$_3$)$_2$

Synthesis of (21)

Boc-Lys(Fmoc)-CO$_2$H (262 mg, 0.56 mmol), N-hydroxysuccinimide (77 mg, 0.67 mmol) and N,N-dicyclohexylcarbodiimide (138 mg, 0.67 mmol) in DMF were stirred at room temperature overnight. DPA-amine (1) (298 mg, 0.51 mmol) in dichloromethane was then added and stirring continued overnight. The product (21) was then purified by silica gel column chromatography eluting with 2 to 5% ammonium hydroxide in acetonitrile (350 mg, 66%). HPLC retention time was 20 minutes using a C8 column with water (solvent A) and acetonitrile (solvent B) containing 0.1% TFA and a gradient to 70% B in 35 minutes with a flow of 1 mL/min.

Synthesis of (22)

Compound (21) (110 mgs, 0.110 mmol) was treated with a solution of 50:50 TFA/CH$_2$Cl$_2$ at room temperature for 1 hour. HPLC using the same system as described in synthesis of (21) showed a single new peak with retention time of 16.1 minutes. The solvent was removed and the residue dissolved in DMF (2 mL) containing DIPEA (100 µL) and FITC (isomer I) (46 mg, 0.117 mmol) added. The mixture was stirred for 3 hours and HPLC was carried out using the method described above, and showed a new peak at 20.4 minutes. The reaction mixture was purified by reverse phase C18 silica gel chromatography using gradient elution from 60% to 90% methanol in water. The isolated yield was 65%.

Synthesis of (23)

Compound (22) (80 mg, 0.60 mmol) was treated with a solution of piperidine in DMF (1:3) for 2 hours. The reaction mixture was then purified by reverse phase C18 column chromatography gradient elution from 30% methanol in water to 70% methanol in water to provide 66 mg (100% yield) of pure (23). HPLC retention time was 14.2 minutes using the HPLC method above. ESI-MS, m/z C$_{63}$H$_{64}$N$_{10}$O$_7$S calcd, 1104.47. Found 1105.00 [M+H]$^+$.

Synthesis of (24)

Reaction of (23) with $^{18}$F-SFB using methods described by Li et al (J. Label. Cmpds. & Radiopharm., 55, 4, 149-154, 2012) followed by treatment with 2 equivalents of zinc nitrate provides (24).

Example 5

In Vitro Studies

This Example illustrates the specificity and efficacy of the Zn-DPA multimodality compounds in vitro.

Cell Line

A U87MG human glioblastoma cell line was obtained from the American Type Culture Collection (Manassas, Va., USA). U87MG glioma cells were grown in Dulbecco's modified medium (USC Cell Culture Core, Los Angeles, Calif., USA) supplemented with 10% fetal bovine serum at 37° C. in humidified atmosphere containing 5% CO$_2$.

MTT Assay

The toxicity of paclitaxel to U87MG cells was determined by a colorimetric assay with 3-(4,5-dimethylthiazol-2-yl)-2,5-diphenyl tetrazolium bromide (MTT; Alfa Aesar). All studies were performed with triplicate samples and repeated at least three times. Briefly, cells were harvested by trypsinization, resuspended in Dulbecco's modified medium, and plated in a 96-well plate at 4,000 cells per well. After treatment with different doses of paclitaxel (ranging from 1 nM to 500 nM) for 16 hours, 22 µL of 0.5 mg/mL sterile filtered MTT was added to each well. The un-reacted dye was removed after 4 hours of incubation, and the insoluble formazan crystals were dissolved in 150 µL of DMSO. The absorbance at 490 nm was measured with a microplate reader (SpectraMax M2e, Molecular Devices, CA). The results demonstrated that U87MG cells are sensitive to paclitaxel treatment.

Figure 3:
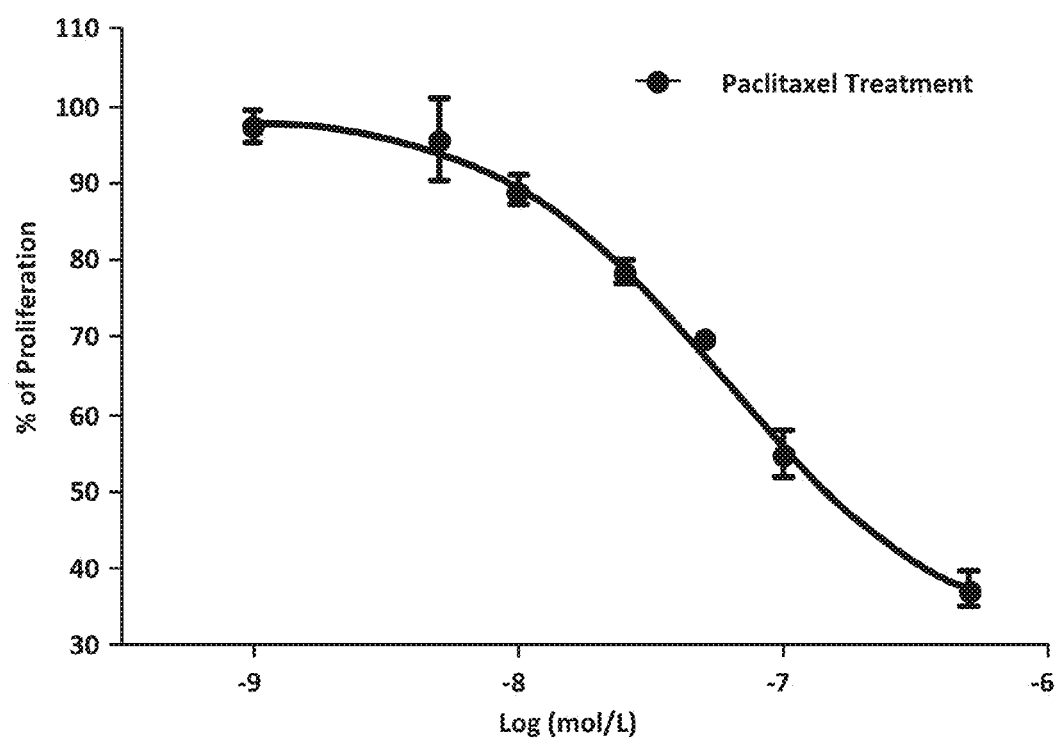
FIG. 3 is a graph illustrating cytotoxicity of paclitaxel on U87MG cells determined by MTT assay, in accordance with various embodiments.

FIG. 3 is a graph illustrating cytotoxicity of paclitaxel on U87MG cells determined by MTT assay. The best-fit 50% inhibitory concentration (IC$_{50}$) values were calculated by fitting the data with nonlinear regression using Graph-Pad Prism 5.0 (Graph-Pad Software, San Diego, Calif.). The IC$_{50}$ value of paclitaxel to the U87MG cells was determined to be 61.4 nM after 16 hours of incubation.

Fluorescence Staining

U87MG cells were seeded in 12-well plates with a density of 2×10$^5$/well. The cells in the treatment group were incubated with paclitaxel (50 nM) for 16 hours. After rinsing twice with phosphate buffered saline (PBS buffer) with 1% BSA, the cells were fixed with 4% paraformaldehyde (PFA) for 20 minutes. The cells were then incubated with 1 mL of Hoechst 33342 (5 µg/mL in PBS) at room temperature for 10 minutes, followed by adding 5 µL of PSVue643 (1 mM) (a Zn-DPA analog with a Cy5 dye attached) and an additional 5 minute incubation. For the blocking study, 500 µL of unlabeled Zn-DPA (1.7 mM) was added into each well with Hoechst 33342. After 10 minutes of incubation, PSVue643 was added to the solution and incubated for 5 minutes at room temperature. The cells were rinsed three times with PBS (with 1% bovine serum albumin (BSA)), and immediately observed with a fluorescence microscope (Nikon ECLIPSE Ti).

Figure 4:
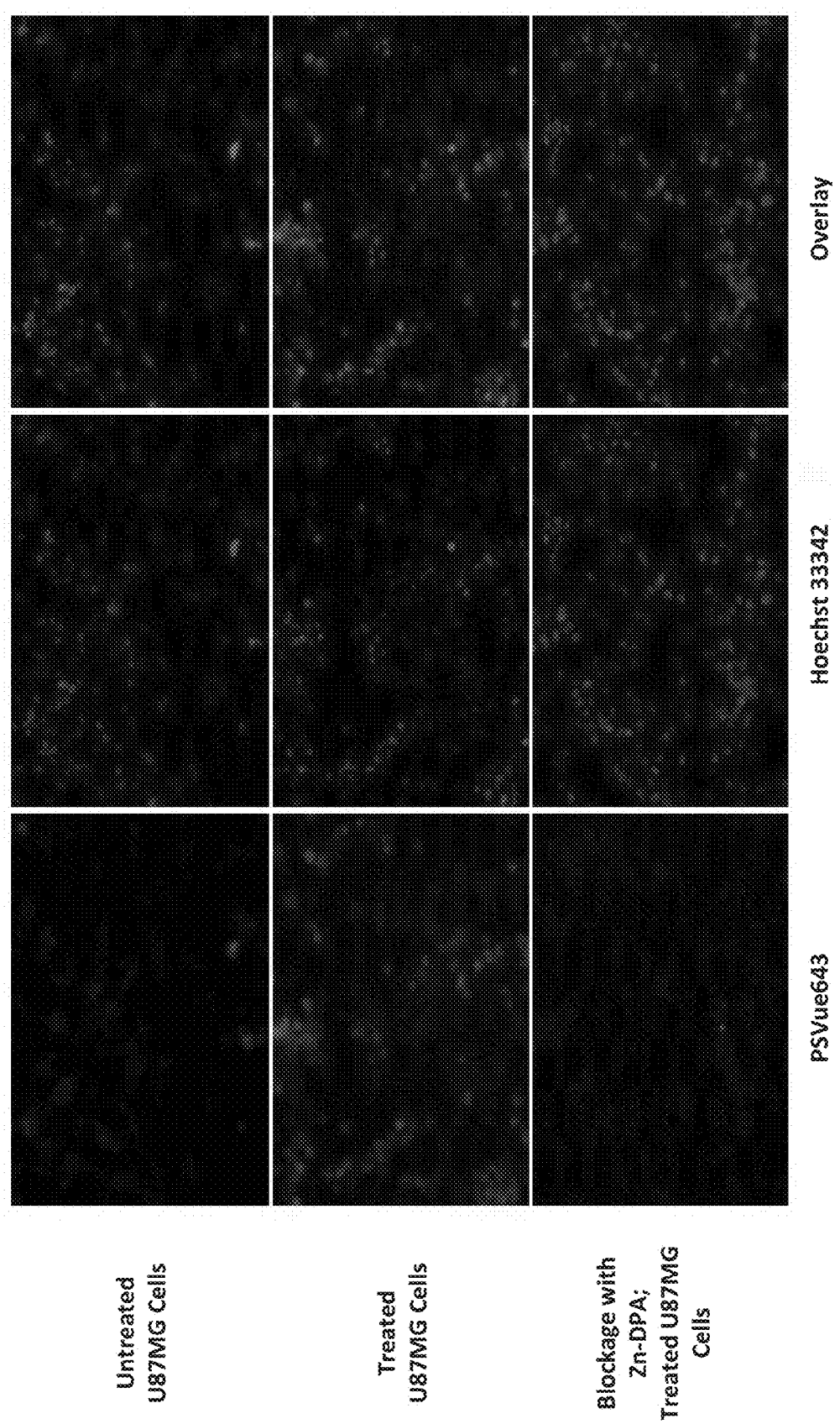
FIG. 4 includes a series of panels illustrating fluorescence staining of U87MG cells with PSVue643 after treatment with 50 nM of paclitaxel for 16 hours (20× magnification), showing co-staining with Hoechst 33342 for nuclei presentation, and with a blockade performed with co-incubation of unlabeled Zn-DPA (5 µM), in accordance with various embodiments.

FIG. 4 includes a series of panels illustrating fluorescence staining of U87MG cells with PSVue643 after treatment with 50 nM of paclitaxel for 16 hours (20× magnification), showing co-staining with Hoechst 33342 for nuclei presentation, and with a blockade performed with co-incubation of unlabeled Zn-DPA (5 µM). The strong red fluorescence signal was identified on the cell membrane and cytoplasm of the treated cells but not on the untreated cells, indicating paclitaxel treatment induced PS exposure. In addition, the fluorescent signal was effectively blocked by co-incubation with excess amount of unlabeled Zn-DPA, indicating that PSVue643 is target-specific binding to the PS.

Confocal Microscopy

U87MG cells were seeded in a 4-well chamber with a density of 5×10$^4$/well. The cells in the treatment group were incubated with 10 nM of paclitaxel for 16 hours. After rinsing three times with PBS buffer, the cells were incubated with 2.5 µL of Hoechst 33342 (2 mg/mL) and 2.5 µL of PSVue643 (1 mM) in 1 mL of PBS for 15 minutes at room temperature. The cells were then rinsed three times with PBS buffer and placed under the LSM 510 confocal laser scanning microscope (Carl Zeiss, Germany).

Figure 5:
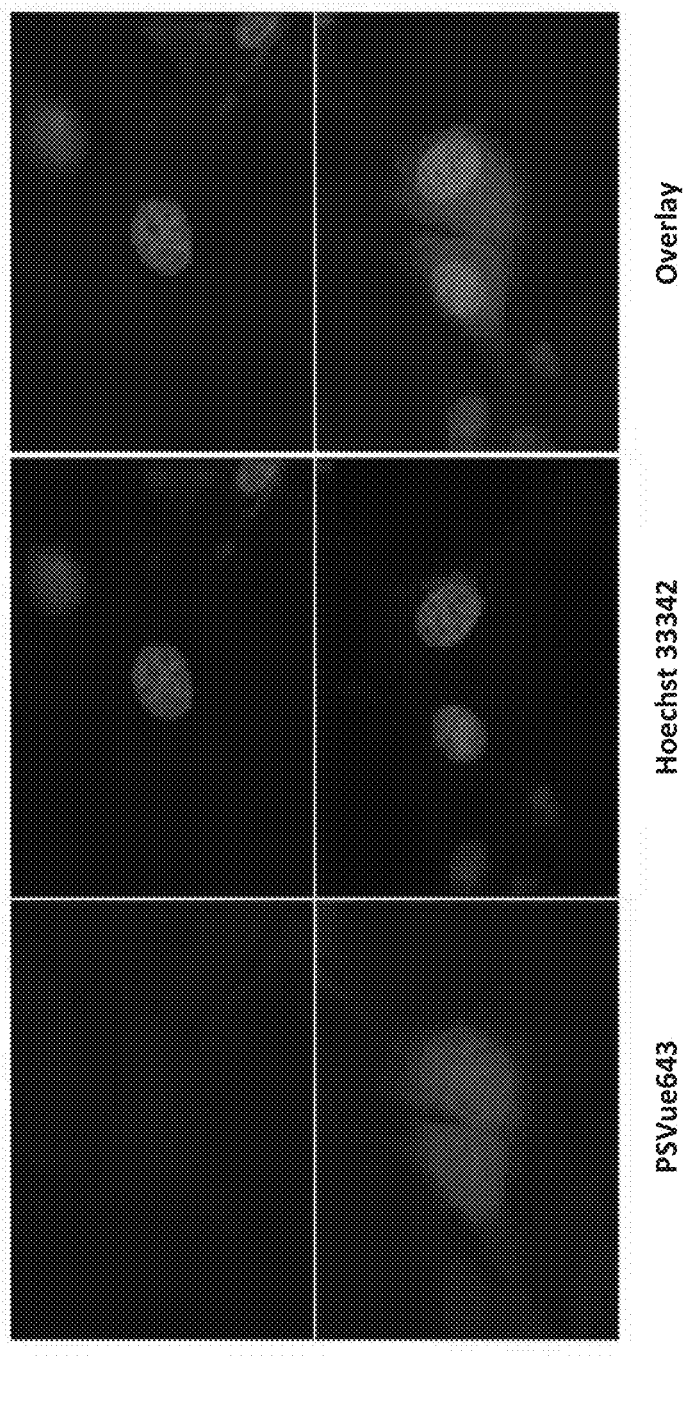
FIG. 5 includes several panels illustrating confocal laser scanning microscope images of untreated U87MG cells (top), and paclitaxel (10 nM) treated U87MG cells (bottom) incubated with PSVue643, showing cytoplasmic distribution of PSVue643 in the treated U87MG cells, in accordance with various embodiments.

FIG. 5 includes several panels illustrating confocal laser scanning microscope images of untreated U87MG cells (top), and paclitaxel (10 nM) treated U87MG cells (bottom) incubated with PSVue643, showing cytoplasmic distribution of PSVue643 in the treated U87MG cells. No PSVue643 staining was observed in the untreated U87MG cells, whereas the PSVue643 deposited throughout the cytoplasm in paclitaxel (10 nM) treated U87MG cells.

Cell Uptake Study

U87MG human glioblastoma cells were seeded into 48-well plates at a density of $1.0 \times 10^5$ cells per well 24 hours prior to the study. U87MG cells were then incubated with 8b (370 kBq/well) at 37° C. for 15, 30, and 60 minutes. After incubation, tumor cells were washed three times with ice cold PBS and harvested by trypsinization with 0.25% trypsin/0.02% EDTA (Invitrogen, Carlsbad, Calif.). At the end of trypsinization, wells were examined under a light microscope to ensure complete detachment of cells. Cell suspensions were collected and measured in a gamma counter (Perkin-Elmer Packard Cobra). Cell uptake data was presented as percentage of total input radioactivity after decay correction. Experiments were performed twice with triplicate wells. After 1 hour of incubation, about 1.5% of 8b was taken up in paclitaxel-treated U87MG cells, which is significantly higher than 0.69% and 0.39% observed for 19b and 17b, respectively (see, e.g., FIG. 6A), indicating that the Zn-DPA moiety is indeed the component binding to PS. The cell uptake of multimodality compound (8b) is 2.18-fold higher than that of single modality compound (19b), and 3.91-fold higher than that of negative control (17b) (see, e.g., FIG. 6B).

Example 6

Animal Model

This Example illustrates the efficacy of the Zn-DPA multimodality compounds at detecting cell death in tumors in an animal model.

Female athymic nude mice (about 4-6 weeks old, with a body weight of 20-25 g) were obtained from Harlan Laboratories (Livermore, Calif.). The U87MG human glioma xenograft model was generated by subcutaneous injection of $5 \times 10^6$ U87MG human glioma cells into the front flank of female athymic nude mice. The tumors were allowed to grow 3-5 weeks until 200-500 $mm^3$ in volume. Tumor growth was followed by caliper measurements of the perpendicular dimensions.

Figure 7C:
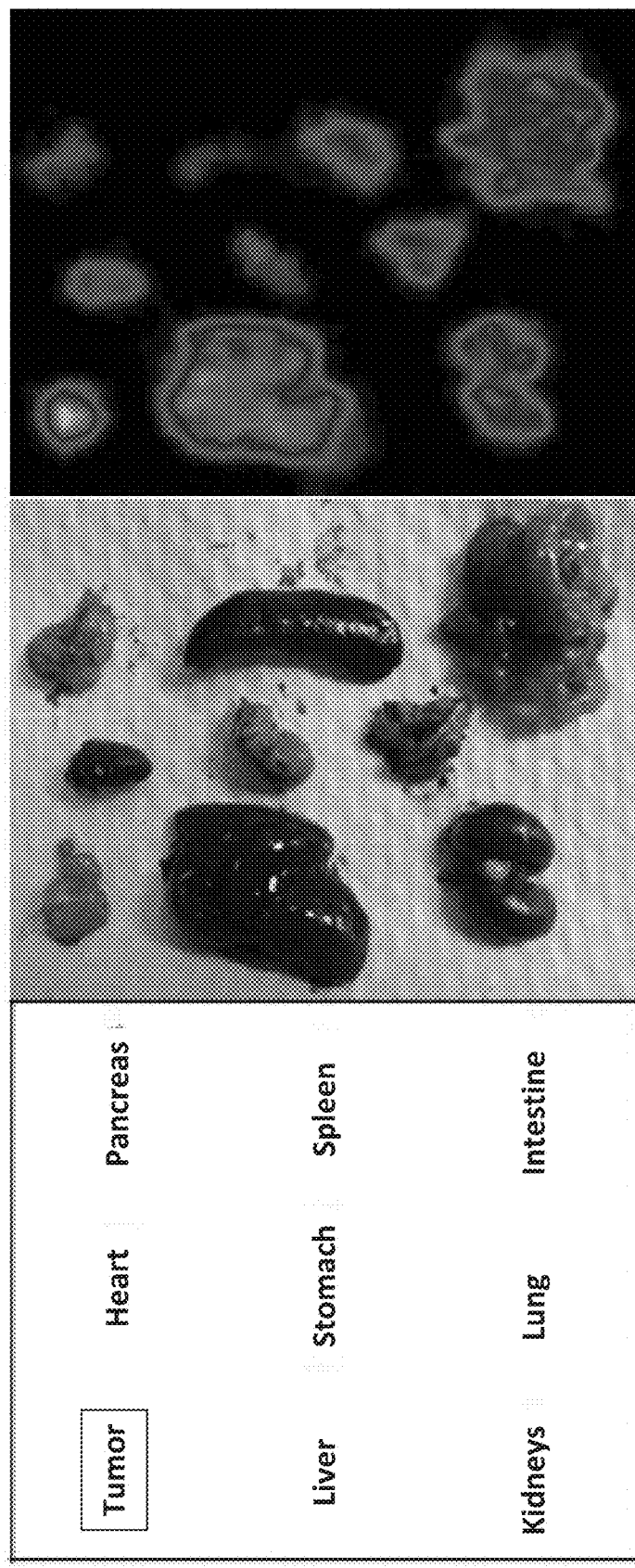
FIG. 7C shows ex vivo PET imaging of tumor and normal tissues of 8b after euthanizing the mice shown in FIG. 7A at 4 hours post-injection, in accordance with various embodiments.

MicroPET scans and imaging analysis were performed using a rodent scanner (microPET R4 scanner; Siemens Medical Solutions). About 7.4 MBq of radiolabeled probe (8b) was intravenously injected into each mouse (n=5) under isoflurane anesthesia. Five-minute static scans were acquired at 1, 2, and 4 hours post-injection. The images were reconstructed by a two-dimensional ordered-subsets expectation maximum (OSEM) algorithm. For each microPET scan, regions of interest were drawn over the tumor, normal tissue, and major organs on the decay-corrected whole-body coronal images. The radioactivity concentration (accumulation) within the tumor, muscle, liver, and kidneys were obtained from the mean value within the multiple regions of interest and then converted to % ID/g. At 4 hours after intravenous injection of radiolabeled probe (8b), mice were sacrificed and dissected. U87MG tumor, major organs, and tissues were collected and scanned using a five-minute static protocol. Representative decay-corrected coronal images at different time points are shown in FIG. 7A. The U87MG tumors were all clearly visible with high contrast to contralateral background at all time points measured beginning 1 hour after injection of 8b. Ex vivo PET imaging of tumor and normal tissues of 8b confirmed the in vivo findings (FIG. 7C).

In vivo fluorescence imaging was performed using the IVIS Imaging System 200 Series and analyzed using the IVIS Living Imaging 4.0 software (PerkinElmer, Hopkinton, Mass., USA). Identical illumination settings (lamp voltage, filters, f/stop, field of views, binning) were used for acquiring all images. Fluorescence emission images were normalized and reported as photons per second per centimeter squared per steradian ($p/s/cm^2/sr$). All near-infrared fluorescence images were acquired using a 1 second exposure time (f/stop=4).

Although certain embodiments have been illustrated and described herein, it will be appreciated by those of ordinary skill in the art that a wide variety of alternate and/or equivalent embodiments or implementations calculated to achieve the same purposes may be substituted for the embodiments shown and described without departing from the scope. Those with skill in the art will readily appreciate that embodiments may be implemented in a very wide variety of ways. This application is intended to cover any adaptations or variations of the embodiments discussed herein. Therefore, it is manifestly intended that embodiments be limited only by the claims and the equivalents thereof.

What is claimed is:

1. A dual-modality pharmaceutical compound, wherein the compound has the structure:

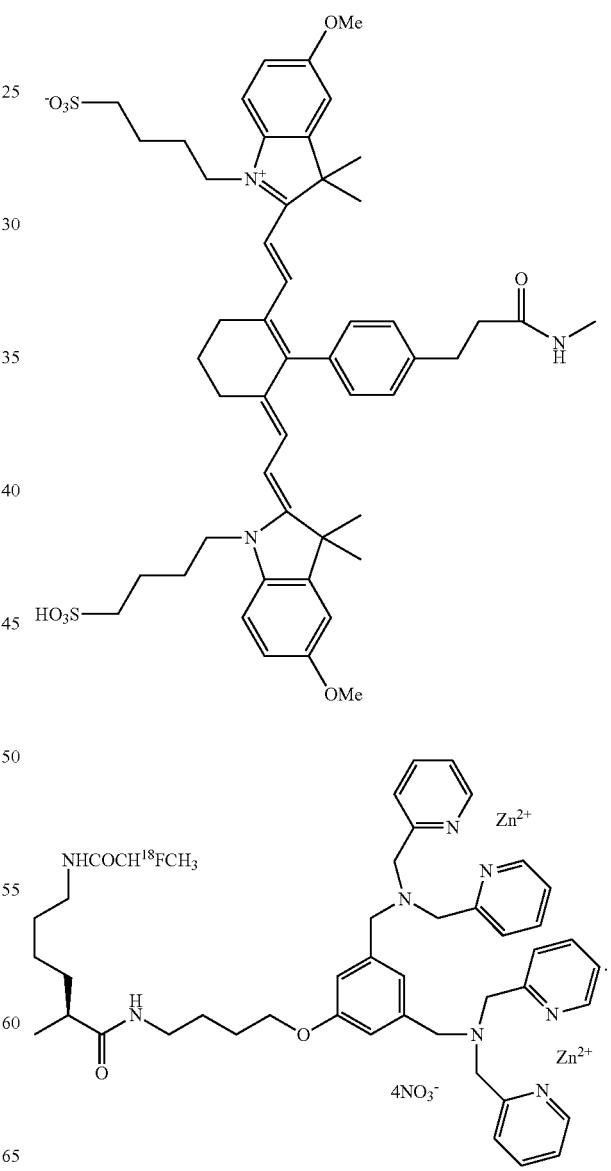

2. A dual-modality pharmaceutical compound, wherein the compound has the structure:
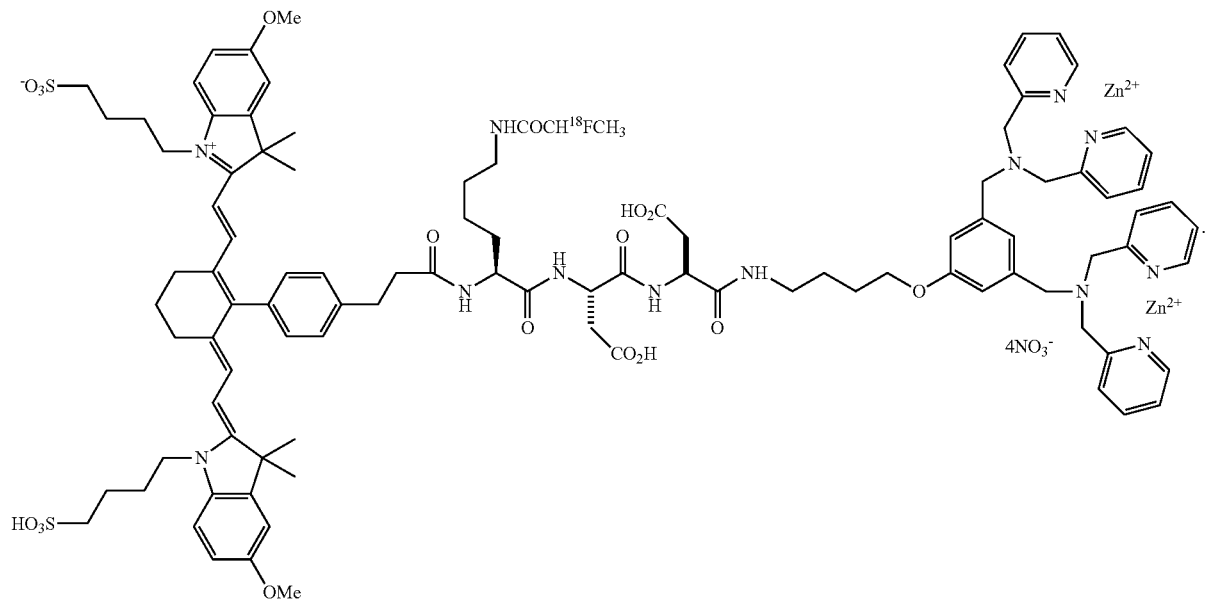
3. A dual-modality pharmaceutical compound, wherein the compound has the structure:
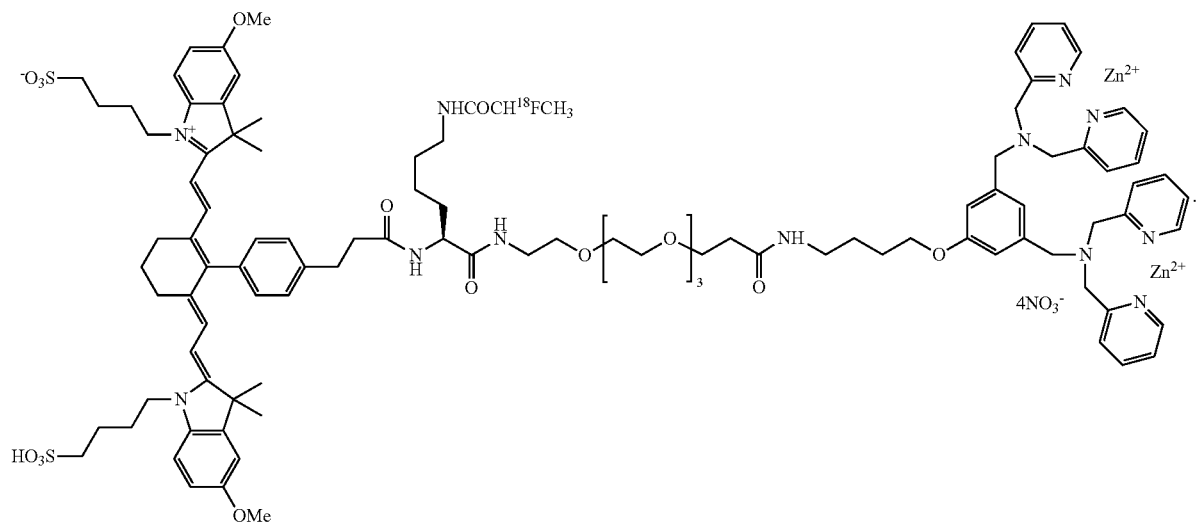

4. A dual-modality pharmaceutical compound, wherein the compound has the structure:
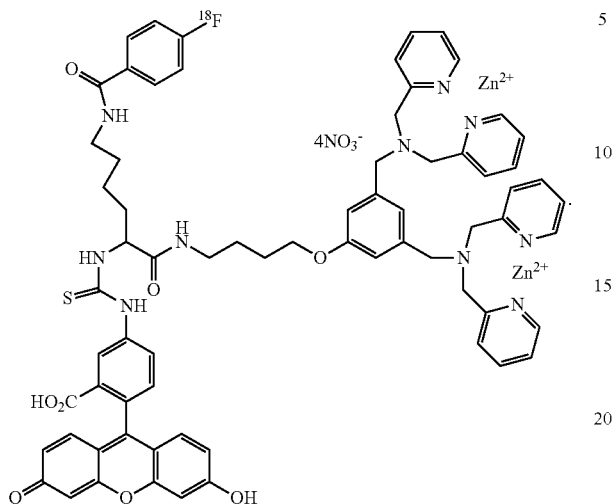
5. A method for monitoring the progression of a tumor, infection, and/or inflammation in a tissue of a subject comprising:
(a) contacting the tissue with a dual-modality pharmaceutical compound selected from the group consisting of
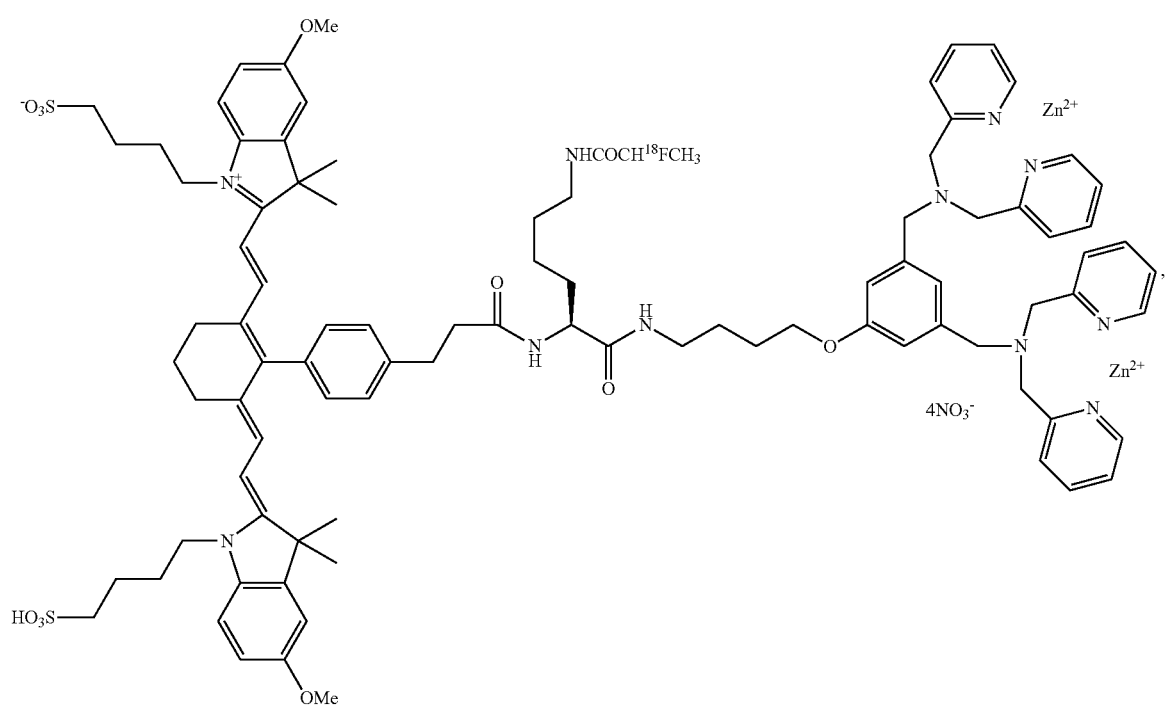

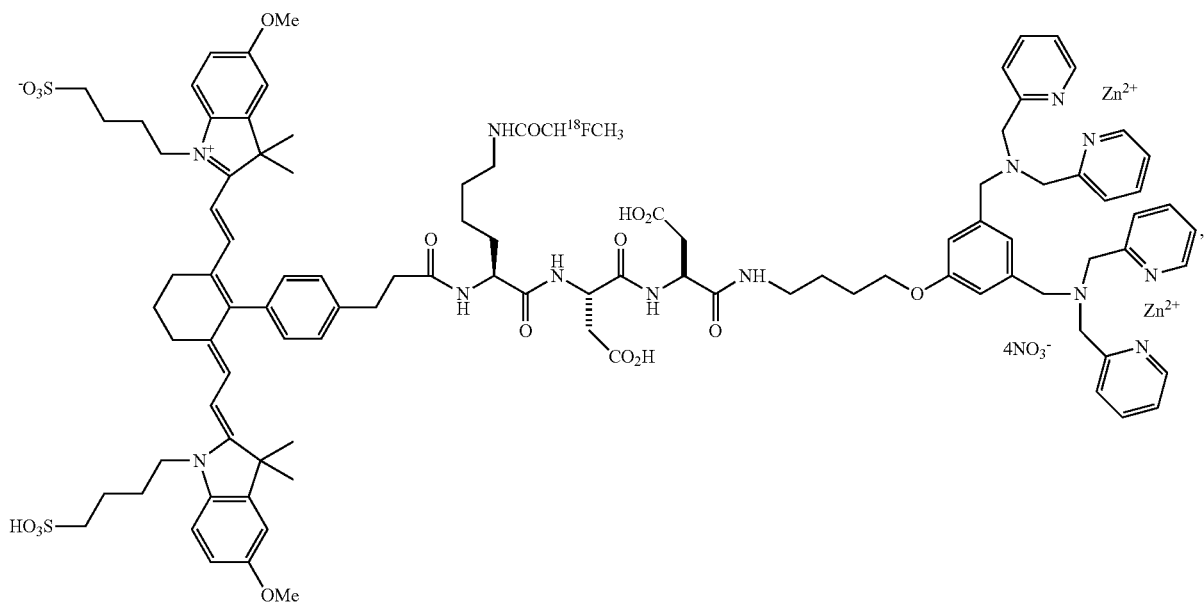
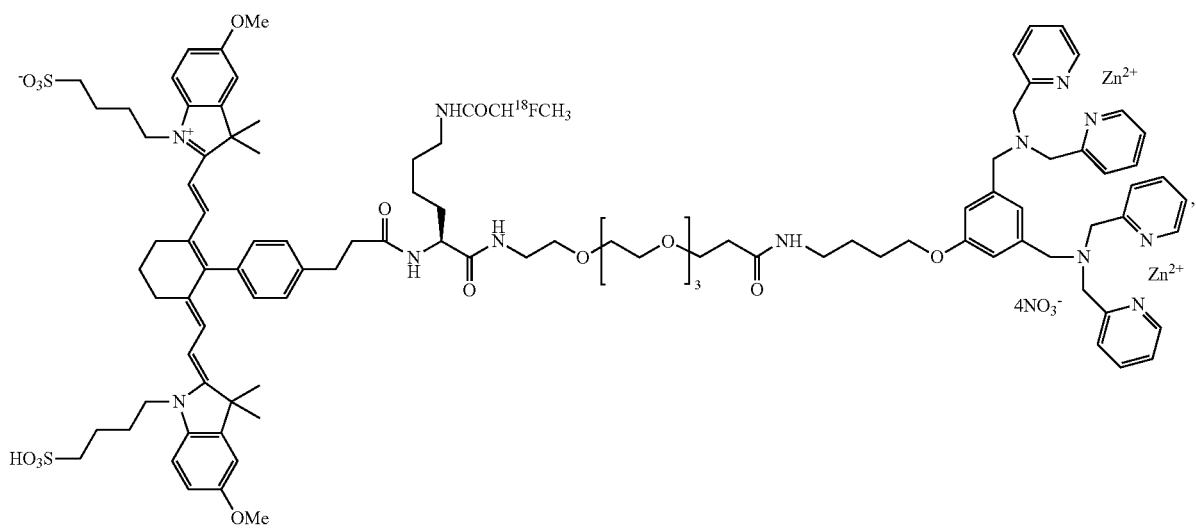

-continued

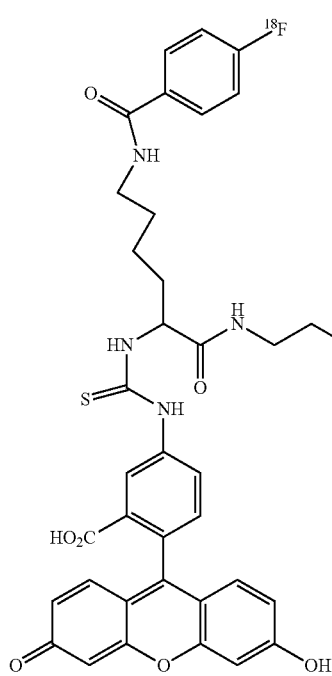
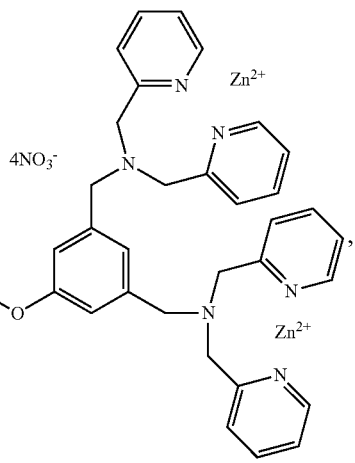

and combinations thereof, and
(b) monitoring binding of the dual-modality pharmaceutical compound in the tissue.

6. The method of claim 5, wherein contacting the tissue with the dual-modality pharmaceutical compound comprises contacting the tissue with the dual-modality pharmaceutical compound in vitro.

7. The method of claim 5, wherein contacting the tissue with the dual-modality pharmaceutical compound comprises contacting the tissue with the dual-modality pharmaceutical compound in vivo.

8. The method of claim 5, wherein monitoring binding of the dual-modality pharmaceutical compound in the tissue comprises monitoring apoptosis.

9. The method of claim 5, wherein contacting the tissue with the dual-modality pharmaceutical compound comprises injecting the subject with the dual-modality pharmaceutical compound.

10. The method of claim 5, wherein monitoring binding of the dual-modality pharmaceutical compound in the tissue comprises both (a) optical imaging and (b) positron emission tomography (PET) or single-photon emission computed tomography (SPECT).

11. The method of claim 5, wherein the infection is a gram positive or gram negative bacterial infection.

12. The method of claim 5, wherein the inflammation is acute or chronic.

13. The method of claim 5, wherein monitoring the progression of a tumor, infection, and/or inflammation in a tissue of a subject comprises:
(a) monitoring the status of the tumor;
(b) monitoring the response of the subject to a treatment; or
(c) assessing an anti-tumor, anti-infection, and/or anti-inflammatory therapy.

* * * * *